US007067265B2

(12) United States Patent
Seino et al.

(10) Patent No.: US 7,067,265 B2
(45) Date of Patent: Jun. 27, 2006

(54) SODIUM ION-DRIVEN CHLORIDE/BI-CARBONATE EXCHANGER

(75) Inventors: Susumu Seino, 22-1-4, Aobanomorinomachi, 638-1 Chibateramachi, Chuo-ku, Chiba-shi, Chiba 260-0844 (JP); Hideki Yano, Chiba (JP); Changzheng Wang, Chicago, IL (US)

(73) Assignees: JCR Pharmaceuticals Co., Ltd., Hyogo (JP); Susumu Seino, Chiba (JP)

( * ) Notice: Subject to any disclaimer, the term of this patent is extended or adjusted under 35 U.S.C. 154(b) by 195 days.

(21) Appl. No.: 10/640,483

(22) Filed: Aug. 14, 2003

(65) Prior Publication Data
US 2004/0063125 A1 Apr. 1, 2004

Related U.S. Application Data

(62) Division of application No. 09/920,804, filed on Aug. 3, 2001, now Pat. No. 6,673,899.

(30) Foreign Application Priority Data
Aug. 9, 2000 (JP) ............................ 2000-241775
Nov. 10, 2000 (JP) ............................ 2000-342911

(51) Int. Cl.
*C12N 15/12* (2006.01)
*G01N 33/566* (2006.01)
(52) U.S. Cl. ................ 435/7.21; 435/69.1; 435/252.3; 435/320.1; 435/536; 435/23.5
(58) Field of Classification Search .................... None
See application file for complete search history.

(56) References Cited

U.S. PATENT DOCUMENTS 6,200,776 B1    3/2001    Boron et al.

FOREIGN PATENT DOCUMENTS

EP    0892052    1/1999

OTHER PUBLICATIONS

Database Em_Hum 'Online? EMBL; Dec. 2, 1998; Grichtchenko et al., "Homo Sapiens Sodium Bicarbonate Cotransporter (NBC) mRNA, complete CDs." retrieved from EBI, accession No. AF069512, Database accession No. AF069512, XP002182615.
Database Swall 'Online?, May 1, 1999; Grichtchenko et al., "Sodium Bicarbonate Cotransporter" retrieved from EBI, accession No. 095233, Database accession No. 095233, XP002182616.
Grichtchenko et al., "Cloning Characterization, and Chromosomal Mapping of a Human Electroneutral Na+-driven CI-HC02 Exchanger", The Journal of Biological Chemistry, vol. 276, No. 11, published Mar. 16, 2001, pp. 8358-8363, XP002182612.
Database EM_RO 'Online? EMBL; Apr. 5, 2000; Wang et al., "Mus musculus sodium bicarbonate cotransporter isoform 3 kNBC-2 mRNA", retrieved from EBI, accession No. AF224508, Database accession No. AF224508, XP002182617.
Database Swall 'Online?, Oct. 1, 2000, Wang et al. "Sodium bicarbonate cotransporter isoform 3 INBC-3" retrieved from EBI, accession No. Q9JKV6, Database accession No. Q9JKV6, XP002182618.
Wang et al., "Mouse Na+:HC03-contransporter isoform NBC-2 (kNBC-3: Cloning, expression, and renal distribution" Kidney International, vol. 59, 2001, pp. 1405-1414, XP002182613.
Burnham et al., "Cloning and functional expression of a human kidney Na+: HC03-cotransporter", The Journal of Biological Chemistry, vol. 272, No. 31, Aug. 1, 1997, pp. 19111-19114, XP002076894.
Database EM_RO 'Online? EMBL; Nov. 15, 22000; Wang et al., "Mus musculus Slc4a10 mRNA for NCBE, complete CDs." retrieved from EBI, accession No. AB033759, Database accession No. AB033759, XP002182619.
Database Swall 'Online?; Mar. 1, 2001; Wang et al., "NCBE", retrieved from EBI, accession No. Q9EST0, Database accession No. Q9EST0, XP002182620.
Database EM_HUM 'Online? EMBL; Nov. 21, 2000; Wang et al., "Homo sapiens SLC4A10 mRNA for NCBE, complete CDs" retrieved from EBI, accession No. AB040457, Database accession No. AB040457, XP002182621.
Database Swall 'Online?; Mar. 1, 2001; Wang et al., "NCBE", retrieved from EBI, accession No. Q9HCQ6, Database accession No. Q9HCQ6, XP002182622.
Wang et al., "The Na+-driven CI-/HC03-exchanger", The Journal of Biological Chemistry, vol. 275, No. 45, published Nov. 10, 2000, pp. 35486-35490, XP002182614.
Boron, W.F. et al., J. Exp. Biol., 200:263-268 (1997).
Pace, C.S. et al., J. Membrane Biol., 73:39-49 (1983).

(Continued)

*Primary Examiner*—John Ulm
(74) *Attorney, Agent, or Firm*—Greenblum & Bernstein, P.L.C.

(57) ABSTRACT

The present invention discloses DNAs comprising nucleotide sequences set forth as SEQ ID NO:1 or NO:3 encoding $Na^+$-driven $Cl^-/HCO_3^-$ exchanger, proteins comprising amino acid sequences set forth as SEQ ID NO:2 or NO:4, and their homologous proteins comprising an amino acid sequence having deletion, substitution, addition or insertion amino acids, which proteins, when expressed in a cell, functions as $Na^+$-driven $Cl^-/HCO_3^-$ exchanger, and cells in which the proteins exogenously expressed.

11 Claims, 5 Drawing Sheets

OTHER PUBLICATIONS

Current Protocols in Molecular Biology, Edited by Ausubel, F.M. et al., John Wiley & Sons, Inc., vol. 1, Chapter 8: Mutagenesis of cloned DNA, pp. 8.0.1-8.5.10.

Vector Essential Data, Gacesa, P. and Ramji, D.P., BIOS Scientific Publishers Limited 1994, John Wiley & Sons in association with BIOS Scientific Publishers Ltd., Expression vectors, pp. 9-12.

Currrent Protocols in Molecular Biology, Edited by Ausubel, F.M. et al., John Wiley & Sons, Inc., vol. 1, Unit 1.8: Introduction of Plasmid DNA into Cells, pp. 1.8.1-1.8.10.

Current Protocols in Molecular Biology, Edited by Ausubel, F.M. et al., John Wiley & Sons, Inc., vol. 1, Chapter 9: Introduction of DNA into Mammalian Cells, pp. 9.0.1-9.17.3.

Current Protocols in Molecular Biology, Edited by Ausubel, F.M. et al., John Wiley & Sons, Inc., vol. 2, Chapter 11: Immunology, pp. 11.0.1-11.16.13.

Burnham, C.E. et al., J. Biol. Chem., 272:19111-19114 (1997).

Inagaki, N. et al., Proc. Natl. Acad. Sci. USA, 91:2679-2683 (1994).

Fukumoto, H. et al., Proc. Natl. Acad. Sci. USA, 85:5434-5438 (1988).

Wang, C.Z. et al., Biochem. Biophys. Res. Commun., 220:196-202(1996).

Thomas. J.A. et al., Zbiochemistry, 18:2210-2218 (1979).

Pushkin, A. et al., J. Biol. Chem., 274:16569-16575 (1999).

Ishibashi, K. et al., Biochem. Biophys. Res. Commun., 24:535-538 (1998).

SODIUM ION-DRIVEN CHLORIDE/BI-CARBONATE EXCHANGER

CROSS-REFERENCE TO RELATED APPLICATION

The present application is a divisional application of U.S. application Ser. No. 09/920,804 filed Aug. 3, 2001 now U.S. Pat. No. 6,673,899, which claims priority under 35 U.S.C. § 119 of Japanese Application Nos. 2000-241775 filed Aug. 9, 2000 and 2000-342911 filed Nov. 10, 2000. The entire disclosure of application Ser. No. 09/920,804 is considered as being part of the disclosure of this application, and the entire disclosure of application Ser. No. 09/920,804 is expressly incorporated by reference herein in its entirety.

FIELD OF THE INVENTION

The present invention relates to human and mouse $Na^+$-driven $Cl^-/HCO_3^-$ exchanger (sodium ion-driven chloride/bicarbonate exchanger) proteins, which are a class of proteins involved in intracellular pH regulation. More specifically, the present invention relates to sodium ion-driven chloride/bicarbonate exchanger proteins, cells designed to express one of the proteins, which cells are of a species different from the origin of the one of the proteins expressed, DNAs encoding the proteins, antibodies to the proteins, and a method for selecting agonists/antagonists of the sodium ion-driven chloride/bicarbonate exchanger proteins.

BACKGROUND OF THE INVENTION

Regulation of intracellular pH ($pH_i$) in response to various stimuli is a critical one among a number of cellular functions. A family of bicarbonate transporters is a major $pH_i$ regulator under physiological conditions in animal cells. Bicarbonate ($HCO_3^-$) transporters are divided into four groups according to their functions [Boron, W. F. et al., J. Exp. Biol., 200:263–268(1997)]: $Na^+$-independent $Cl^-/HCO_3^-$ exchanger (alternatively called an anion exchanger, AE), $Na^+$-$HCO_3^-$ cotransporter (NBC), $K^+$-$HCO_3^-$ cotransporter, and $Na^+$-driven $Cl^-/HCO_3^-$ exchanger. Three AEs and three NBCs have been cloned and functionally characterized, but the molecular structure of the $K^+$-$HCO_3^-$ cotransporter and the $Na^+$-driven $Cl^-/HCO_3^-$ exchanger have remained unknown.

A $Na^+$-driven $Cl^-/HCO_3^-$ exchanger was first discovered in invertebrate neurons and was later found in vertebrate neurons as well as non-neuronal cells, including brain, vascular endothelial cells, sperm, kidney and pancreatic β-cells. $Na^+$-driven $Cl^-/HCO_3^-$ exchanger is an intracellular pH regulator that transports extracellular $Na^+$ and $HCO_3^-$ into the cells in exchange for intracellular $Cl^-$, thereby playing an important role in cellular alkalinization.

In pancreatic, β-cells, glucose is the most important physiological regulator of insulin secretion. Glucose metabolism induces an increase in intracellular pH in the pancreatic cells. It has been shown that this glucose-induced $pH_i$ rise is evoked primarily by the action of $Na^+$-driven $Cl^-/HCO_3^-$ exchanger [Pace, C. S. et al., J. Membrane Biol., 73:39–43(1983)].

$Na^+$-driven $Cl^-/HCO_3$-exchanger is thus an important intracellular pH regulator in various cells, but its molecular basis is not known. Analysis of the molecular structure and function of $Na^+$-driven $Cl^-/HCO_3^-$ exchanger should be valuable not only for functional analysis of insulin secretion by pancreatic β-cells but also for screening as well as for drug designing based on its molecular structure aimed at the development of therapeutics of diabetes mellitus.

On the above background, the present invention has as its objective to clone $Na^+$-driven $Cl^-/HCO_3^-$ exchangers, thereby obtaining their DNA for sequencing, providing cells of a different species expressing the DNAs, and determining the structure and function of the $Na^+$-driven $Cl^-/HCO_3^-$ exchangers.

SUMMARY OF THE INVENTION

Thus, the present invention provides a $Na^+$-driven $Cl^-/HCO_3^-$ exchanger protein comprising the amino acid sequence set forth as SEQ ID NO:2 or NO:4 in the Sequence Listing.

The present invention further provides a protein comprising an amino acid sequence having deletion, substitution, addition or insertion of one or more amino acids relative to the amino acid sequence set forth as SEQ ID NO:2 or NO:4 in the Sequence Listing and which, when expressed in a cell, functions as $Na^+$-driven $Cl^-/HCO_3^-$ exchanger.

The present invention further provides an above protein wherein the $Na^+$-driven $Cl^-/HCO_3^-$ exchanger, dependently upon both of extracellular bicarbonate and intracellular chloride ions, takes up extracellular sodium ion into the cell and transport intracellular sodium ion out of the cell.

The present invention further provides a cell in which one of the above proteins is expressed, wherein the cell is of a species different from the species of origin of the one of the proteins. Non-limiting examples of such cells of different species include *Xenopus laevis* oocytes and HEK293 cells. Expression of a $Na^+$-driven $Cl^-/HCO_3^-$ exchanger in such cells of different species may be achieved by transfection of a DNA encoding the $Na^+$-driven $Cl^-/HCO_3^-$ exchanger or by introduction of a cRNA corresponding to the $Na^+$-driven $Cl^-/HCO_3^-$ exchanger.

The present invention further provides antibodies to the above proteins. The antibodies may be monoclonal or polyclonal.

The present invention further provides a method for selection of agonists and antagonists of $Na^+$-driven $Cl^-/HCO_3^-$ exchanger, which method comprises bringing a cell of a different species expressing the protein into contact with a candidate compound, measuring the function of the $Na^+$-driven $Cl^-/HCO3$- exchanger, comparing the result thus obtained with a result obtained by measuring the function of the sodium ion-driven chloride/bicarbonate exchanger of the cell which has not been brought into contact with the candidate compound, and thereby determining whether or not the candidate compound enhances or inhibits the function.

The present invention further provides a DNA comprising the nucleotide sequence set forth as SEQ ID NO:1 or NO:3 in the Sequence Listing, a DNA comprising a nucleotide sequence consisting of nucleotides 67 through 3330 in the nucleotide sequence set forth as SEQ ID NO:1 in the Sequence Listing, and a DNA comprising a nucleotide sequence consisting of the nucleotides 83 through 3346 in the nucleotide sequence set forth as SEQ ID NO:3 in the Sequence Listing.

The present invention further provides a DNA comprising a nucleotide sequence having deletion, substitution, addition or insertion of one or more nucleotides relative to a DNA comprising a nucleotide sequence consisting of the nucleotides 67 through 3330 in the nucleotide sequence set forth as SEQ ID NO:1 in the Sequence Listing, and encoding:

(1) a protein comprising the amino acid sequence set forth as SEQ ID NO:2 in the Sequence Listing, or (2) a protein comprising an amino acid sequence having deletion, substitution, addition or insertion of one or more amino acids relative to the amino acid sequence set forth as SEQ ID NO:2 in the Sequence Listing, which protein, when expressed in a cell, functions as $Na^+$-driven $Cl^-/HCO_3^-$ exchanger.

The present invention still further provides a DNA comprising a nucleotide sequence having deletion, substitution, addition or insertion of one or more nucleotides relative to a DNA comprising a nucleotide sequence consisting of the nucleotides 83 through 3346 in the nucleotide sequence set forth as SEQ ID NO:3 in the Sequence Listing, and encoding:

(1) a protein comprising the amino acid sequence set forth as SEQ ID NO:4 in the Sequence Listing, or (2) a protein comprising an amino acid sequence having deletion, substitution, addition or insertion of one or more amino acids relative to the amino acid sequence set forth as SEQ ID NO:4 in the Sequence Listing, which protein, when expressed in a cell, functions as $Na^+$-driven $Cl^-/HCO_3^-$ exchanger.

The present invention further provides a protein comprising an amino acid sequence having deletion, substitution, addition or insertion of one to three amino acids relative to the amino acid sequence set forth as SEQ ID NO:2 or NO:4 in the Sequence Listing, with amino acids 479~499, 514~534, 564~584, 693~713, 733~753, 780~800, 826~846, 882~901, 905~924, and 972~992 of the amino acid sequence set forth as SEQ ID NO: 2 or SEQ ID NO: 4 kept intact, which protein, when expressed in a cell, functions as $Na^+$-driven $Cl^-/CO_3^-$ exchanger and wherein the cell is of a species different from the species of origin of the protein consisting of the amino acid sequence set forth as SEQ ID NO: 2 or SEQ ID NO: 4.

The present invention further provides an isolated DNA comprising a nucleotide sequence having deletion, substitution, addition or insertion of one to ten nucleotides relative to a DNA comprising a nucleotide sequence consisting of the nucleotides 67 through 3330 in the nucleotide sequence set forth as SEQ ID NO:1 in the Sequence Listing, and encoding:

(1) a protein comprising the amino acid sequence set forth as SEQ ID NO:2 in the Sequence Listing, or (2) a protein comprising an amino acid sequence having deletion, substitution, addition or insertion of one to three amino acids relative to the amino acid sequence set forth as SEQ ID NO:2 in the Sequence Listing, with amino acids 479~499, 514~534, 564~584, 693~713, 733~753, 780~800, 826~846, 882~901, 905~924, and 972~992 of the amino acid sequence set forth as SEQ ID NO: 2 kept intact, which protein, when expressed in a cell, functions as $Na^+$-driven $Cl^-/CO_3^-$ exchanger.

The present invention still further provides an isolated DNA comprising a nucleotide sequence having deletion, substitution, addition or insertion of one to ten nucleotides relative to an isolated DNA comprising a nucleotide sequence consisting of the nucleotides 83 through 3346 in the nucleotide sequence set forth as SEQ ID NO:3 in the Sequence Listing, and encoding:

(1) a protein comprising the amino acid sequence set forth as SEQ ID NO:4 in the Sequence Listing, or (2) a protein comprising an amino acid sequence having deletion, substitution, addition or insertion of one to three amino acids relative to the amino acid sequence set forth in SEQ ID NO:4 in the Sequence Listing, with amino acids 479~499, 514~534, 564~584, 693~713, 733~753, 780~800, 826~846, 882~901, 905~924, and 972~992 of the amino acid sequence set forth as SEQ ID NO: 4 kept intact, which protein, when expressed in a cell, functions as $Na^+$-driven $Cl^-/CO_3^-$ exchanger.

DETAILED DESCRIPTION OF THE INVENTION

Figure 1:
FIG. 1 shows RNA blot analysis of NCBE mRNA in rat tissues and hormone-secreting cell lines (a) and RT-PCR detection of NCBE mRNA from mouse pancreatic islets (b).
Figure 1:
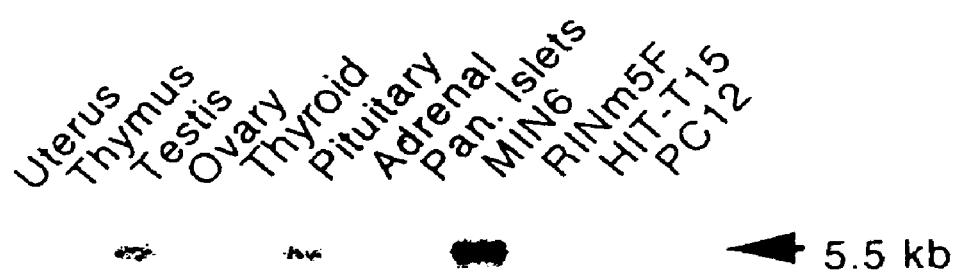
Figure 1:
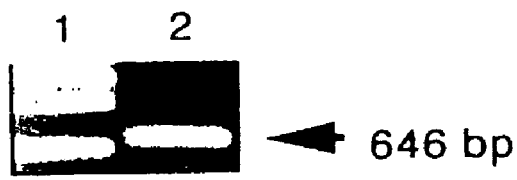

In the present invention, the cells of different species in which the protein of the present invention is expressed may be, for example, *Xenopus laevis* oocytes or HEK293 cells, and selected according to a given purpose from a variety of cells other than those from mouse or human. A conventional method well known in the art may be used for bringing about expression of a protein of the present invention in cells of species different from the species of origin of the protein.

In the present specification, the term "one or more" when used in the context of "an amino acid sequence having deletion, substitution, addition or insertion of one or more amino acids" means a number of one to ten in general, and preferably a number of one to a few (e.g., three or four).

Also in the present specification, the term "one or more" when used in the context of "a DNA comprising a nucleotide sequence having deletion, substitution, addition or insertion of one or more nucleotides" means a number of one to ten in general, and preferably a number of one to a few (e.g., three or four).

A variety of such mutant DNAs, as well as mutant proteins encoded by the DNAs, can be produced by means of recombinant DNA technology. First, mutations can be introduced into a cloned DNA fragment through any of different chemical or enzymatic processes. Mutant DNAs thus obtained are then sequenced for selection of particular mutants with intended merits. This method allows systematic preparation of different mutants regardless of their phenotypes. General methods for preparing mutant clones are as follows.

1. With the help of an oligonucleotide, substitution, deletion, insertion or addition of one or more nucleotides can be directly induced in a given DNA sequence. This method allows introduction of a number of mutations into a small region of a given DNA.

2. By using a relatively long oligonucleotide, a desired gene can be synthesized.

3. By means of region-specific mutagenesis, a desired mutation can be introduced into a large (1–3 kb) DNA region.

4. Linker-scanning mutagenesis of DNA is a method suitable to introduce a cluster point mutation into a relatively small (4–10 bp) DNA region.

5. PCR is also utilized as a method for directly introducing a mutation. [References: Current protocols in molecular biology. 3 vols., Edited by Ausubel F. M. et al., John Wiley & Sons, Inc., Current Protocols., Vol. 1, Chapter 8: Mutagenesis of cloned DNA, pages 8.0.1–8.5.10]

Also well known to those skilled in the art are methods for preparing plasmids or other vectors which can express a desired gene including different mutations obtained by the above methods. That is, by inserting a DNA comprising a desired gene into an expression vector DNA using a combination of restriction enzymes and a ligase, a recombinant plasmid is readily constructed which carries the desired gene. The recombinant plasmid thus obtained is then introduced into different cells to effect transfection, thereby producing transformed cells. A range of cells may be utilized, from prokaryotic cells, e.g. *E. coli*, to yeast, insect, plant and animal cells. [Reference: Vectors essential data. Gacesa P. and Ramji D. P. 166 pages. BIOS Scientific Publishers Limited 1994., John Wiley & Sons in association with BIOS Scientific Publishers Ltd. Expression vectors, pages 9–12.]

Introduction of a recombinant plasmid into host cells may be carried out by calcium chloride method or by electroporation. Calcium chloride method is an efficient way for achieving transformation and it does not requires any apparatus specially designed for it. If still higher efficiency is needed, electroporation is recommended.

[References: Current Protocols in Molecular Biology, 3 Vols. Edited by Ausbel F. M. et al., John Wiley & Sons, Inc., Current Protocols, Vol. 1, unit 1.8: Introduction of Plasmid DNA into Cells, pages 1.8.1–1.8.10]

There are known two types of transfection generally carried out on animal cell lines, i.e., a transient type and a stable and permanent type. In transient transfection, transformed cells are cultured for 1–4 days to allow transcription and replication of the introduced gene, and then the cells are harvested and their DNA analyzed. In many studies, alternatively, a stable transformant cell line is produced, in which the introduced gene is incorporated into the chromosomes. Examples of the method for transfection include calcium phosphate method, electroporation, and liposome fusion method.

[Reference: Current protocols in molecular biology. 3 vols. Edited by Ausubel F. M. et al., John Wiley & Son, Inc., Current Protocols. Vol. 1, chapter 9: Introduction of DNA into mammalian cells, pages 9.0.1–9.17.3.]

Polyclonal and monoclonal antibodies to the $Na^+$-driven $Cl^-/HCO_3^-$ exchanger proteins of the present invention, or to their fragments or their analogues, are readily prepared using technologies well known in the art. Antibodies thus obtained may be used, for example, in immunohistochemistry of $Na^+$-driven $Cl^-/HCO_3^-$ exchanger protein expressed in cells of different species or for inhibition of its function by blocking the protein. Cells of different species in which the function of $Na^+$-driven $Cl^-/HCO_3^-$ exchanger is inhibited are used as a control in selection of agonists/antagonists of the protein.

A general method for preparing a monoclonal antibody in mg-scale directed to the $Na^+$-driven $Cl^-/HCO_3^-$ exchanger proteins of the present invention is as follows: Mice are inoculated with one of the antigen proteins to immunize. The spleen is removed from the mice exhibiting a sufficient antibody titer. The spleen cells are dissociated and B cells are selected and fused with myeloma cells of B cell origin to form hybridoma cells secreting the antibody. The monoclonal antibody secreted by the hybridoma cells is purified from the culture medium by using an affinity column, or by ion-exchange or gel filtration, etc. Polyclonal antibody of the present invention may also be prepared by a conventional method: using rabbits, horses, mice or guinea pigs as immunized animals, the antigen protein is inoculated along one of the schedules known in the art to immunize the animals, and then an immunoglobulin such as IgG is isolated from the collected serum.

[Reference: Current protocols in molecular biology, 3 vols. Edited by Ausubel F. M. et al., John Wiley & Sons, Inc., Current Protocols, Vol. 2, chapter 11: Immunology, pages 11.0.1–11.16.13.]

EXAMPLES

The present invention is described in further details with reference to examples. However, it is not intended that the present invention be limited to the examples.

To determine its structure and functional role, the present inventors cloned a $Na^+$-driven $Cl^-/HCO_3^-$ exchanger (designated NCBE) from cDNA library from MIN6, an insulin secreting mouse cell line. The primary structure, tissue distribution and functional characterization of $Na^+$-driven chloride ($Cl^-$)/bicarbonate ($HCO_3^-$) exchanger (NCBE) will be described below.

It was revealed that the mouse NCBE protein (SEQ ID NO:2) consists of 1,088 amino acids and has 65, 65 and 41% amino acid identity to the sodium bicarbonate cotransporter from human muscle, retina and kidney, respectively. The mouse NCBE has was found to have ten putative membrane spanning regions and the conserved 4,4'-diisothiocyanostilbene-2,2'-disulfonic acid (DIDS)-binding motif characteristic of anion exchangers and sodium bicarbonate cotransporters. NCBE mRNA is was shown to be expressed at high levels in the brain and in a mouse insulinoma cell line MIN6, and, though at low levels, also in pituitary, testis, kidney, and ileum. Through functional analysis of NCBE protein expressed in *Xenopus laevis* oocytes and HEK293 cells, it was demonstrated that the protein causes a rise in intracellular pH by transporting extracellular $Na^+$ and $HCO_3^-$ into cells in exchange for intracellular $Cl^-$. Based on the findings, the present inventors concluded that the cloned NCBE is the $Na^+$-driven $Cl^-/HCO_3^-$ exchanger that regulates intracellular pH in native cells.

Then, to also identify a human NCBE, a partial sequence (2,746 bp) of the mouse $Na^+$-driven $Cl^-/HCO_3^-$ exchanger cDNA obtained above was first amplified by PCR. For this amplification, a DNA fragment having the sequence consisting of the nucleotides 250–270 of the sequence set forth as SEQ ID NO:1 in the Sequence Listing was used as a sense primer, and, as an antisense primer, a DNA fragment having a sequence complementary to the sequence consisting of the nucleotides 2976–2995 of the sequence set forth as SEQ ID NO:1 in the Sequence Listing. PCR conditions were as follows:
Initial denaturation: 94° C., 2 min
Amplification (20 cycles)
denaturation: 94° C., 15 sec
annealing: 60° C., 30 sec
extension: 72° C., 2 min
Final extension: 72° C., 7 min The PCR product thus obtained was labeled with $^{32}$P-dCTP by nick translation and used to screen about 1 million phages from a human fetal brain cDNA library (Clontech). Four positive phage clones were obtained and their DNAs were digested with EcoRI. After agarose electrophoresis, corresponding bands were excised, and respective DNAs extracted to obtain inserts. Separately, pGEM7Z (Promega) was digested with EcoRI and treated with alkaline phosphatase. To this, the inserts obtained from the positive phages were ligated, respectively, for subcloning. The respective inserts were then sequenced on an autosequencer (ABI 310), and, based on the sequences thus obtained, the cDNA nucleotide sequence corresponding to human NCBE protein was determined (set forth as SEQ ID NO:3). According to the result, the sequence of human NCBE protein then was determined (set forth as SEQ ID NO:4 in the Sequence Listing).

The methods and results of the above experiments will be described below, focusing on the procedures followed and results obtained with mouse NCBE.

[Materials and Methods]

<cDNA Cloning>

A partial cDNA fragment of human kidney NBC cDNA [Burnham, C. E., et al., J. Biol. Chem., 272:19111–19114 (1997)] amplified by PCR, using a human kidney cDNA as a template. The sense and antisense primers used in this were 5'-TTTGGAGAAAACCCCTGGT-3' (nt 2232–2250) (SEQ ID NO:5) and 5'-TGACATCATCCAGGAAGCTG-3' (nt 2912–2931) (SEQ ID NO:6). PCR was performed up to 40 cycles under the following conditions: denaturation at 94° C. for 15 sec, annealing at 60° C. for 30 sec, and extension at 72° C. for 45 sec in a thermal cycler GeneAmp PCR system 9600 (PE Applied Biosystems, Foster, Calif.). The 700 bp-PCR product was subjected to screening of a MIN6 cDNA library [Inagaki, N., et al., Proc. Natl. Acad. Sci. USA, 91:2679–2683(1994)] as a probe under a low stringent condition previously described [Fukumoto, H. et al., Proc. Natl. Acad. Sci. USA, 85:5434–5438(1988)]. Positive clones were subcloned in pGEM-3Z vector (Promega, Madison, Wis.) and sequenced in both directions using ABI PRISM™ 377 DNA sequencer (PE Applied Biosystems).

<RNA Blot Analysis>

RNA blot analysis was performed using 10 µg of total RNA from various tissues and cells. The RNAs were denatured with formaldehyde, electrophoresed on 1% agarose gel, and transferred onto a nylon membrane. The blots were probed with NCBE cDNA under a standard condition previously described [Wang, C-Z. et al., Biochem. Biophys. Res. Commun., 220:196–202(1996)]. Before autoradiography, the blots were washed with 0.1×SSC and 0.1% SDS at room temperature for one hr and then at 50° C. for another hour.

<Reverse Transcription Polymerase Chain Reaction (RT-PCR)>

Total RNA was prepared from isolated mouse pancreatic islets with TRIZOL Reagent (Life Technologies, Inc., Rockvill, Md.). First-strand cDNA (10 ng) was generated using Superscript™ II reverse transcriptase (Life Technologies) with random primers. PCR was performed with Expand High Fidelity PCR System (Roch Diagnostics, Mannheim, Germany) using about 1 ng of template DNA in a 20 µl reaction volume under a standard condition. The sense and antisense primers used were 5'-GTCATGTTAGACCAA-CAGGT-3' (nt 4283–4302) (SEQ ID NO:7) and 5'-GTTG-TAATAGCGACACTC-3' (nt 4911–4928) (SEQ ID NO:8). The PCR product was resolved on 1% agarose gel and confirmed by DNA sequencing.

<Functional Analysis of NCBE in *Xenopus laevis* oocytes>

The coding sequence of NCBE in pSD5 was linearized by digestion with FspI and in vitro transcribed with SP6 RNA polymerase as previously described (Wang, C-Z. et al., Biochem. Biophys. Res. Commun., 220:196–202(1996)). Defolliculated oocytes were injected with NCBE cRNA (50 nl, 0.5 µg/µl) or water and incubated in 1×MBS medium (88 mM NaCl, 1 mM KCl, 0.8 mM $MgCl_2$, 0.4 mM $CaCl_2$, 0.3 mM $Ca(NO_3)_2$, 2.4 mM $NaHCO_3$ and 7.5 mM Tris, pH 7.4) for 3–5 days at 18° C. before the studies. The oocytes were preincubated for one hr at 18° C. in the standard solution (100 mM NaCl, 2 mM KCl, 1 mM $MgCl_2$, 1 mM $CaCl_2$, and 8 mM $NaHCO_3$, pH 7.4).

For studies of dependency on extracellular $Na^+$ concentration, the oocytes were then incubated in 1.4 ml of either 1, 10, 30 or 100 mM $Na^+$ solution bubbled with 1.5% $CO_2$, pH 7.4 with 0.074 MBq of $^{22}Na^+$ (NEN™ Life Science Products, Boston, Mass.). In each solution, the $Na^+$ in the standard solution was substituted with an equal molar amount of choline. A ten µl aliquot was removed from the incubation solution for later determination of $^{22}Na^+$-specific activity. After 15 min, $^{22}Na^+$ uptake was terminated by three washes with an ice-cold solution containing 1, 10, 30 or 100 mM $Na^+$, pH 7.4, respectively, and the oocytes were then lyzed in 0.5 ml of 5% SDS and 4.5 ml of Aqueous Counting Scintillant (Amersham Pharmacia Biotech) was added. $^{22}Na^+$ uptake was performed in either $Cl^-$-free 1, 10, 30 or 100 mM $Na^+$ solution (pH 7.4). Extracellular $Cl^-$ was substituted with an equal molar amount of gluconic acid, and extracellular $Na^+$ was substituted with an equal molar amount of N-methyl-D-glucamine (NMG). The $^{22}Na^+$ uptake for 15 min was also examined in the presence or absence of 300 µM 4,4'-diisothiocyanostilbene-2,2'-disulfonic acid (DIDS, Sigma), an inhibitor of anion-transporters in the standard solution.

For the study of dependency on extracellular $HCO_3^-$ concentration, $Na^+$ uptake experiments were performed in 1, 3, 10 or 30 mM $HCO_3^-$ solutions bubbled with 1.5% $CO_2$ at 18° C., pH 7.4, including 0.074 MBq of $^{22}Na^+$. The solutions contained 2 mM KCl, 1 mM $MgCl_2$ and 1 mM $CaCl_2$, pH 7.4, and further 107 mM NaCl and 1 mM $NaHCO_3$ for 1 mM $HCO_3^-$ solution, 105 mM NaCl and 3 mM $NaHCO_3$ for 3 mM $HCO_3^-$ solution, 98 mM NaCl and 10 mM $NaHCO_3$ for 10 mM $HCO_3^-$ solution, and 78 mM NaCl and 30 mM $NaHCO_3$ for 30 mM $HCO_3^-$ solution.

For $^{36}Cl^-$ efflux experiment, the oocytes were preincubated for one hour in the $Cl^-$-free solution for depletion of intracellular $Cl^-$, or $Cl^-$ containing standard solution. The oocytes were incubated in 0.074 MBq of $^{36}Cl^-$-containing solution (NEN™ Life Science Products) at 18° C. for one hour bubbling with 1.5% $CO_2$. The oocytes were rapidly washed three times with the corresponding, respective solutions and then transferred into 1.5 ml of each a $Cl^-$-free solution bubbled with 1.5% $CO_2$, pH 7.4. A 10 µl aliquot was removed from the incubation solution for later determination of $^{36}Cl^-$ specific activity. $^{36}Cl^-$ activities in the solution were measured at 0, 5, 15, 25 and 35 min. The oocytes were treated as described above for the measurement of the remaining intracellular $^{36}Cl^-$. Portions of the medium from respective time points were counted and the values were summed to determine flux. $^{36}C^-$ efflux was presented as a percent relative to the total cellular $^{36}Cl^-$ released. $^{22}Na^+$ and $^{36}Cl^-$ activities were measured with beta scintillation counter (Aloka, Japan).

<Functional Analysis of NCBE in HEK293 Cells>

HEK293 cells were plated at a density of $3 \times 10^5$ cells per 3.5 cm-diameter dish containing a coverslip, and cultured in Dulbecco's modified Eagle's medium (DMEM, high glucose) supplemented with 10% fetal bovine serum, streptomycin (60.5 μg/ml), and penicillin (100 μg/ml) at 37° C. under a humidified condition of 95% air and 5% $CO_2$. Cells were transfected with 1 μg of the full-length NCBE cDNA in the pcDNA3.1 vector (Invitrogen, Groningen, The Netherlands) using Lipofectamine, Lipofectamine Plus, and Opti-MEM I reagents (Life Technologies, Gaithersburg, Md.) according to the manufacturer's instructions. The cells were studied 48–72 hours after transfection. Changes in intracellular pH were monitored using 2',7'-bis-(2-carboxyethyl)-5-(6)-carboxyfluorescein, acetoxymethyl ester (BCECF-AM, Molecular Probe, Eugene, Oreg.) (Burnham, C. E., et al., J. Biol. Chem., 272:19111–19114(1997)). HEK293 cells were loaded with 1 μM BCECF-AM for one hour and monitored for changes in intracellular pH by dual-excitation wavelength method with a computerized image processor (490 nm/450 nm; 520–560 nm emission) (Argus-50; Hamamatsu Photonics, Hamamatsu, Japan). $^-\Delta pH_i$ was determined as the difference between the intracellular pH before and 10 min after switching to the test solution. The $pH_i$ calibration curve was generated using KCl/nigericin technique (Thomas, J. A. et al., Biochemistry 18:2210–2218(1979)). In all the experiments, the cells were first acidified by $NH_4^+$-prepulse with 40 mM NH4Cl-containing solution for 5 min before switching to the $Na^+$-containing respective test solutions (Burnham, C. E., et al., J. Biol. Chem., 272:19111–19114(1997)).

To estimate $Na^+$-dependency of the intracellular pH ($\Delta pH_i$) recovery from intracellular acidification, a $Na^+$-free solution (115 mM tetramethylammonium chloride (TMA-Cl), 25 mM $KHCO_3$, 0.8 mM $K_2HPO_4$, 0.2 mM $KH_2PO_4$, 1 mM $CaCl_2$, 1 mM $MgCl_2$, 10 mM HEPES) and a $Na^+$-containing solution (TMA-Cl and $KHCO_3$ in the $Na^+$-free solution were replaced with 90 mM NaCl, 25 mM KCl, and 25 mM $NaHCO_3$) were used.

To test for $HCO^-$-dependency, a $HCO_3^-$-free, $Na^+$-free solution (115 mM TMA-Cl, 0.8 mM $K_2HPO_4$, 0.2 mM $KH_2PO_4$, 1 mM $CaCl_2$, 1 mM $MgCl_2$, 10 mM HEPES) and a $HCO_3^-$-free, $Na^+$-containing solution (in which TMA-Cl in the $HCO_3^-$-free, $Na^+$-free solution was replaced with 90 mM NaCl and 25 mM KCl) were used.

To determine $Cl^-$-dependency, a $Cl^-$-free, $Na^+$-free solution (25 mM $KHCO_3$, 0.8 mM $K_2HPO_4$, 0.2 mM $KH_2PO_4$, 10 mM HEPES, 115 mM NMG-gluconate) and a $Cl^-$-free, $Na^+$-containing solution (in which NMG-gluconate was replaced with 115 mM sodium gluconate) were used and the results were compared with each other.

All the solutions were bubbled with 95% $O_2$ and 5% $CO_2$, and their pH adjusted to 7.4. The osmolarity of each solution was adjusted with sucrose. The assays were carried out at 37° C.

<Statistical Analysis>

The results were expressed as means±SE. Statistical significance between experiments was determined by Student's t test.

[Results and Discussion]

NCBE is structurally related to $Na^+$-$HCO_3^-$ transporters.

As described above, the cDNA encoding $Na^+$-driven $Cl^-$/$HCO_3^-$ exchanger (NCBE) was cloned from a MIN6 cDNA by screening it using a partial human kidney $Na^+$-$HCO_3^-$ cotransporter (NBC) cDNA as a probe. The thus determined nucleotide sequence (NCBE) is set forth as SEQ ID NO:1 in the Sequence Listing. The composite 5,385-bp nucleotide sequence contains an open reading frame, which follows an in-frame termination signal upstream of the "ATG" and encodes a protein of 1,088 amino acids set forth as SEQ ID NO:1 having a predicted molecular weight of 122 kDa. A hydrophobicity analysis indicates that the amino acid sequence has putative membrane spanning segments (TM1 to TM 10) at the following positions, respectively.

TM1: amino acids 479~499
TM2: amino acids 514~534
TM3: amino acids 564~584
TM4: amino acids 693~713
TM5: amino acids 733~753
TM6: amino acids 780~800
TM7: amino acids 826~846
TM8: amino acids 882~901
TM9: amino acids 905~924
TM10: amino acids 972~992

In the amino acid sequence, there are three potential N-linked glycosylation sites in the extracellular loops between the third (TM3) and fourth (TM4) spanning region (Asn-647, Asn-657 and Asn-667). Putative DIDS-binding motif is at amino acids 815–818.

Comparison of amino acid sequence between NCBE and other NBCs showed that NCBE has 65%, 65% and 41% amino acid identity to human muscle NBC [Pushkin, A. et al., J. Biol. Chem., 274:16569–16575(1999)], human retina NBC [Ishibashi, K. et al., Biochem. Biophys. Res. Commun., 24:535–538(1998)], and human kidney NBC [Burnham, C. E., et al., J. Biol. Chem., 272:19111–19114(1997)], respectively. This indicates that NCBE represents a novel bicarbonate transporter. The amino acid sequences in the putative transmembrane regions and DIDS-binding motif Lys Leu Lys Lys (residue 815–818) are well conserved in NCBE, while those in the intracellular amino- and carboxyl-terminal regions and in the large extracellular loop between the third and the fourth membrane spanning regions are rather divergent.

NCBE is expressed at high levels in the brain and insulin-secreting clonal pancreatic β-cells.

RNA blot analysis revealed a 5.5 kb NCBE mRNA is expressed at high levels in brain and the insulin secreting cell line MIN6 cells and expressed at low levels in pituitary, testis, kidney, and ileum (FIG. 1, a). RT-PCR analysis shows that NCBE is also expressed in pancreatic islets (FIG. 1, b).

In the figure, "a" represents the result of the RNA blot analysis of NCBE mRNA in rat tissues and hormone-secreting cell lines. The size of hybridized transcripts is indicated. "b" represents the results of RT-PCR detection of NCBE mRNA in mouse pancreatic islets. DNA length markers and RT-PCR products are shown in lanes 1 and 2, respectively.

NCBE is a $Na^+$-driven $Cl^-$/$HCO_3^-$ exchanger that regulates intracellular pH ($pH_i$).

The present inventors examined the functional properties of NCBE using *Xenopus laevis* oocyte system. $^{22}Na^+$ uptake and $^{36}Cl^-$ efflux were measured 3–5 days after injection of the cRNAs or water (control). Bubbling with 1.5% $CO_2$ to acidify the oocytes, the present inventors first examined the effect of extracellular $Na^+$ concentration on $^{22}Na^+$ uptake. The results are shown in FIG. 3.

Figure 3:
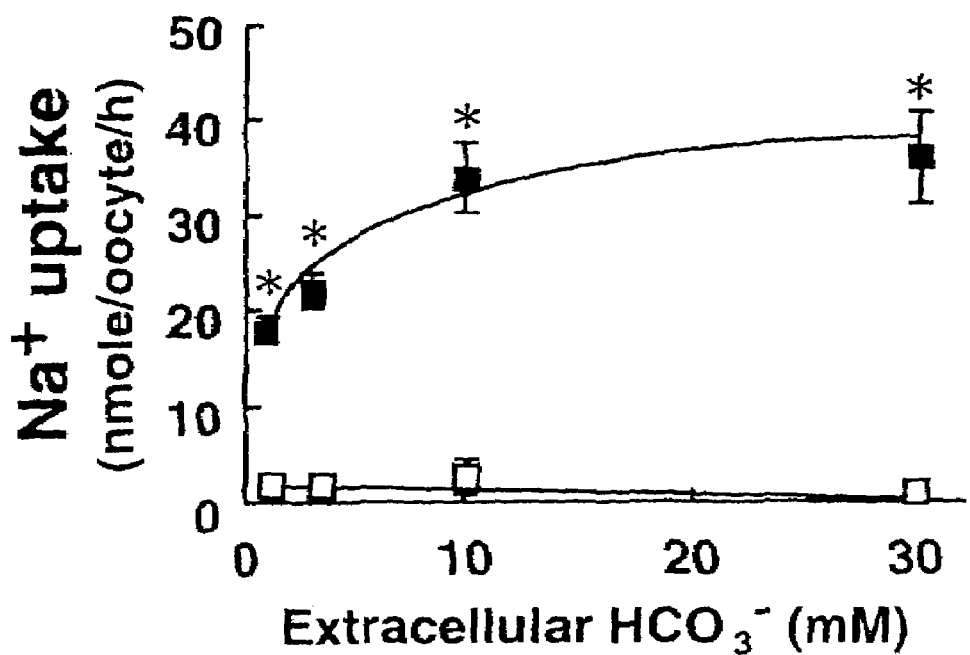
FIG. 3 shows a graph illustrating the effect of extracellular $HCO_3^-$ concentration on $^{22}Na^+$ uptake.

FIG. 3 illustrates the relation between $^{22}Na^+$ uptake (nmol/oocyte/hour) and extracellular $Na^+$ concentration. In the figure, ■ and ● indicate the results obtained with the cells injected with NCBE cRNA, and □ and ○ the results obtained with the cells injected with water. ■ and □ indicate the results obtained using $Cl^-$-containing extracellular solutions, and ● and ○ indicate the results obtained using $Cl^-$-free extracellular solutions. The respective data represent the mean±SE (standard error) for 7 to 16 oocytes from two independent experiments. * and † ($p<0.05$) indicate the presence/absence of statistical significance in the difference from water-injected cells and from incubation in $Cl^-$-free extracellular solutions, respectively, with 10, 30 or 100 mM $Na^+$.

Figure 2:
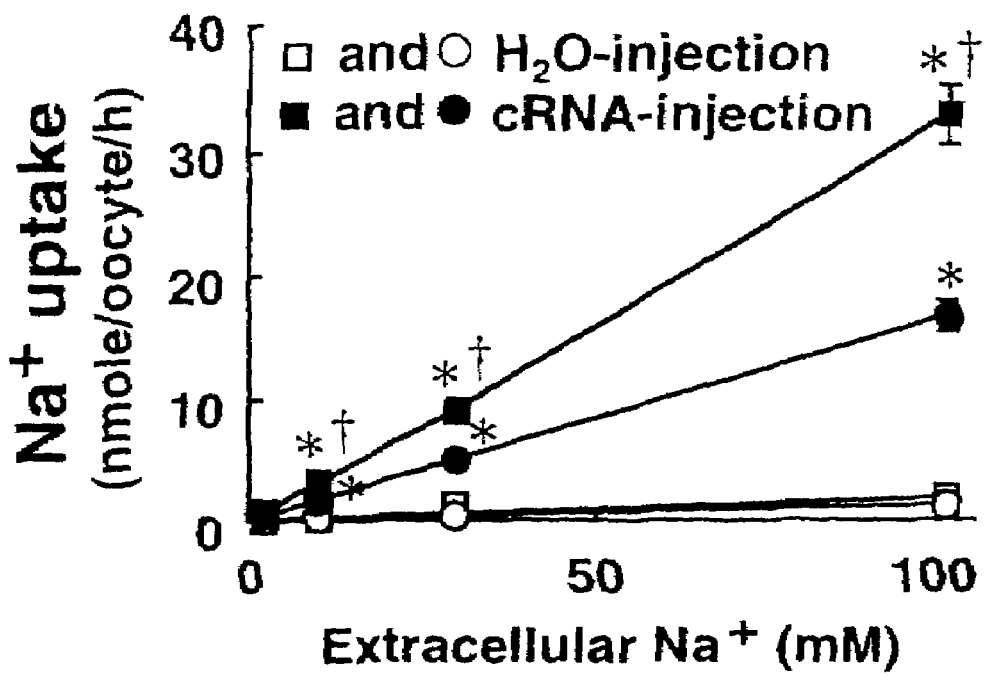
FIG. 2 shows a graph illustrating the effect of extracellular $Na^+$ concentration on $^{22}Na^+$ uptake.

As shown in FIG. 2, the increase in $^{22}Na^+$ uptake was dependent on extracellular $Na^+$ concentrations, with a linear pattern observed in NCBE cRNA-injected oocytes over the physiological range of $Na^+$ concentrations. The water-injected oocytes showed no increase in $^{22}Na^+$ uptake. Comparison of $Na^+$ uptake between the results obtained with $Cl^-$-containing and $Cl^-$-free solutions showed significantly higher $Na^+$ uptake in the presence of extracellular $Cl^-$ than the in the absence of extracellular $Cl^-$ (FIG. 2). These results indicate that NCBE transports extracellular $Na^+$ into the cells and that extracellular $Cl^-$ participates in acceleration of the NCBE's activity.

The present inventors, then, examined the effect of extracellular bicarbonate ion on $^{22}Na^+$ uptake. The results are shown in FIG. 3. The respective data represent the mean±SE (standard error) for 11 to 16 oocytes from two independent experiments. * ($p<0.05$) indicates comparison with water-injected cells. As evident from the figure, increased extracellular bicarbonate ion significantly boosted $Na^+$ uptake in a concentration-dependent manner in the NCBE cRNA-injected oocytes, while the water-injected oocytes did not show any such change in $Na^+$ uptake. These results indicate that extracellular bicarbonate ion is necessary in transporting $Na^+$ into the cells.

Figure 4:
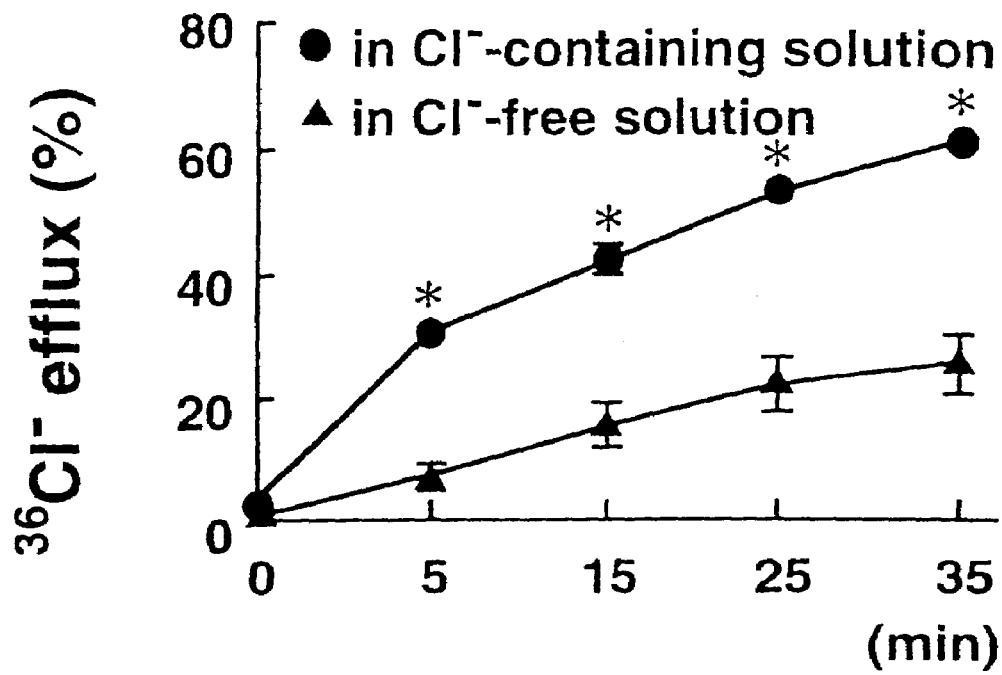
FIG. 4 shows a graph illustrating the effect of intracellular $Cl^-$ on $^{36}Cl^-$ efflux.

To determine whether $Cl^-$ is transported into or out of the cells by NCBE, the present inventors examined $^{36}Cl^-$ efflux from *Xenopus laevis* oocytes. As $36Cl^-$ influx was not detected in water-injected oocytes, analysis was made only for $^{36}Cl^-$ efflux from NCBE cRNA-injected oocytes. The rate (%) of $^{36}Cl^-$ efflux from NCBE cRNA-injected oocytes was measured from 0 to 35 min under the intracellular $Cl^-$-depleted condition by preincubation with a $Cl^-$-free solution and under the intracellular $Cl^-$ non-depleted condition by preincubation with $Cl^-$-containing solution. The results are shown in FIG. 4. In the figure, ● indicates the results obtained with cells under the intracellular $Cl^-$ non-depleted condition (preincubation in the $Cl^-$-containing solution), and ▲ indicates the results obtained with cells under the intracellular $Cl^-$-depleted condition (preincubation in the $Cl^-$-free solution). The data represent the mean±SE (standard error) for 16 to 17 oocytes from three independent experiments. * ($p<0.05$) indicates comparison with intracellular $Cl^-$-depleted cells, at 5, 15, 25, and 35 min.

Comparison made among results of $^{36}Cl^-$ efflux under the different conditions indicates that NCBE transports intracellular $Cl^-$ out of the cells. Taken together, these results demonstrate that NCBE exchanges extracellular $Na^+$ and bicarbonate ion with intracellular $Cl^-$.

Figure 5:
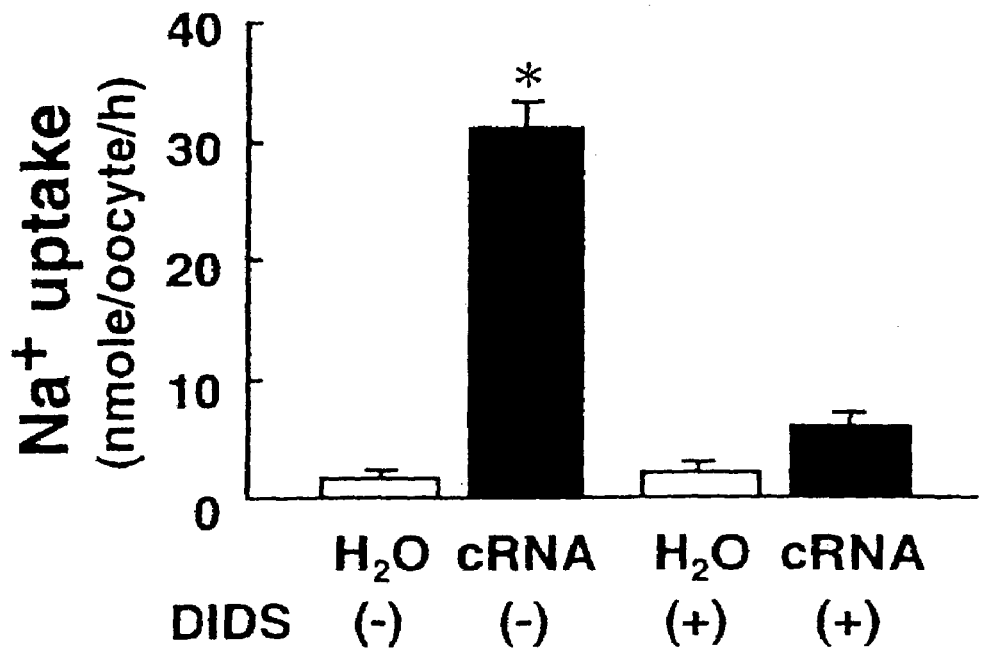
FIG. 5 shows a graph illustrating the effect of DIDS on $^{22}Na^+$ uptake.

The present inventors also examined the effect of DIDS, an inhibitor of anion-transporter, on $^{22}Na^+$ uptake. Expression was assessed in the absence or presence of 0.3 mM DIDS. The results are shown in FIG. 5. The data represent the mean±SE (standard error) for 21 to 22 oocytes from three independent experiments. * ($p<0.05$) indicates comparison with cRNA+DIDS.

While the $^{22}Na^+$ uptake in NCBE cRNA-injected oocytes was 31.4±2.1 nmol/oocyte/hour (n=21) in the absence of DIDS, it was 6.0±0.7 nmol/oocyte/hour (n=14) in the presence of 300 μM DIDS. In water-injected oocytes, the uptake was 1.6±0.3 (n=22) and 2.1±0.4 (n=19) nmol/oocytes/hour in the absence and presence of DIDS, respectively. Thus, DIDS was shown to partially inhibit $^{22}Na^+$ uptake by NCBE (FIG. 5).

Figure 6:
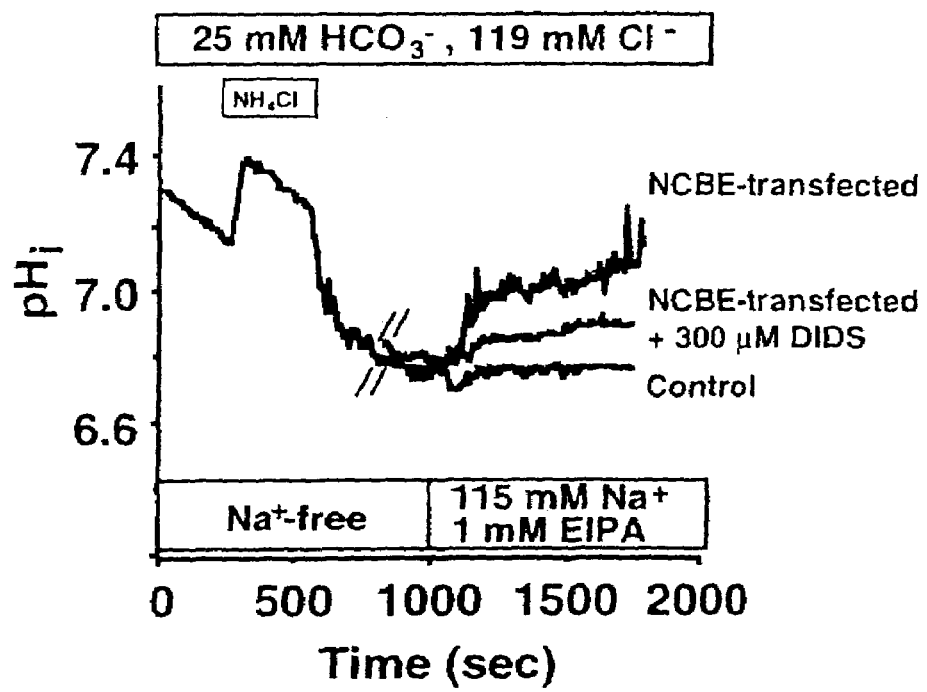
FIG. 6 shows a graph illustrating the change in the intracellular pH in the presence and absence of 300 μM DIDS, along with the change in the intracellular pH in control (non-transfected) cells.

To clarify the role of NCBE in the regulation of intracellular pH, changes in intracellular pH were measured under various conditions using HEK293 cells transiently transfected with NCBE. All the experiments were performed under conditions where the intracellular pH was acidified with $NH_4^+$ prepulse. To determine whether the change in the intracellular pH is dependent on extracellular $Na^+$, the environment of the cells was switched from a $Na^+$-free solution to a $Na^+$-containing solution. The results are shown in FIG. 6. FIG. 6 is a graph illustrates a trace of control (non-transfected) cells and NCBE-transfected cells with or without 300 μM DIDS. The environment of the cells was switched from a $Na^+$-free solution to a $Na^+$-containing solution.

As shown in the figure, a rapid recovery of intracellular pH ($\Delta pH_i$) was observed only in the NCBE-transfected cells in the presence of 1 mM 5-(N-ethyl-N-isopropyl)-amiloride (EIPA), a specific inhibitor of $Na^+/H^+$ exchanger ($\Delta pH_i$ was 0.239±0.028 (n=97) in the NCBE-transfected cells and 0.003±0.015 (n=70) in the control. $p<0.05$) (FIG. 6). This recovery in intracellular pH was partially inhibited by 300 μM DIDS ($\Delta pH_i$ was 0.023±0.042 (n=89). $p<0.05$).

Figure 7:
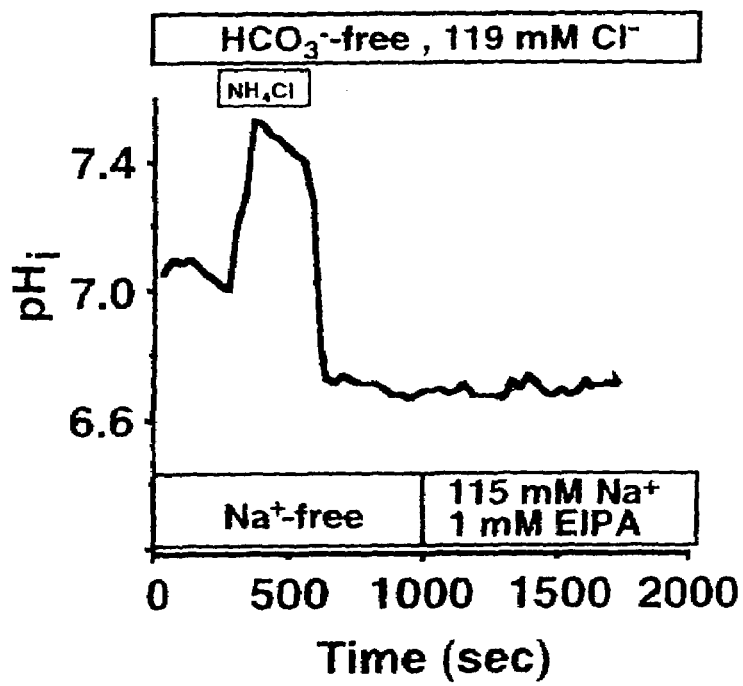
FIG. 7 shows a graph illustrating the change observed in the intracellular pH when the environment is switched from a $Na^+$-free solution to a $Na^+$-containing solution, under a $HCO_3^-$-free condition.

To determine whether this change in intracellular pH is bicarbonate ion-dependent, the environment of the NCBE-transfected cells was switched from a $HCO_3^-$-free, $Na^+$-free solution to a $HCO_3^-$-free but $Na^+$-containing solution, in the presence of 1 mM EIPA. However, as shown in FIG. 7, no recovery of intracellular pH was detected ($\Delta pH_i$ was 0.002±0.014 (n=71)).

Figure 8:
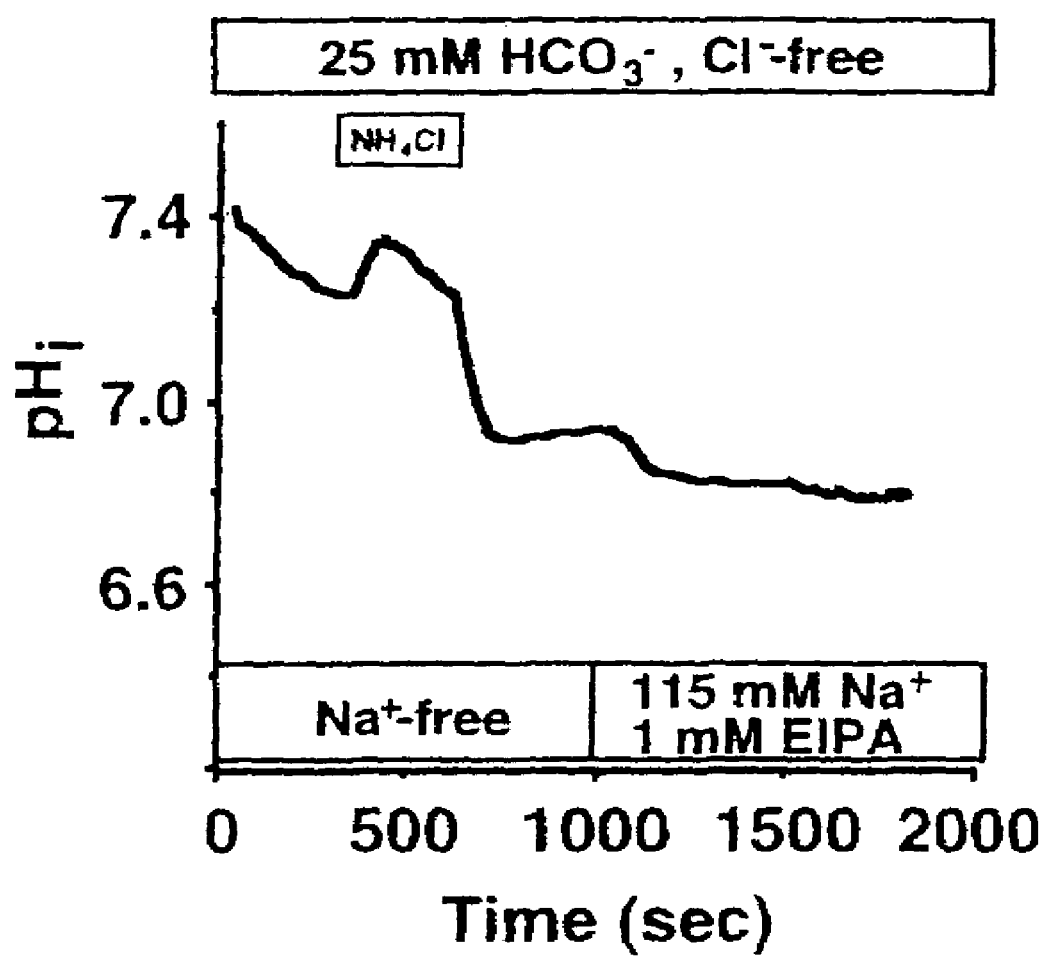
FIG. 8 shows a graph illustrating the change observed in the intracellular pH when the environment is switched from a $Na^+$-free solution to a $Na^+$-containing solution, under a $Cl^-$-free condition.

Finally, an examination for $Cl^-$ dependency was also made by the present inventors. NCBE-transfected cells were kept in a $Cl^-$-free solution (under an intracellular $Cl^-$-depletion condition) throughout the experiments. Under this condition, the environment of the cells was switched from a $Na^+$-free solution to a $Na^+$-containing solution. In the presence of 1 mM EIPA, as shown in FIG. 8, no recovery of intracellular pH was detected [$\Delta pH_i$ was 0.067±0.012 (n=95)].

These results indicate that recovery of intracellular pH from intracellular acidification is detected only where extracellular $Na^+$ and $HCO_3^-$ and intracellular $Cl^-$ are present.

The studies of the function of NCBE heterologously expressed in *Xenopus laevis* oocytes and HEK293 cells show that NCBE allows intracellular pH to recover from acute intracellular acidification, by transporting extracellular $Na^+$ and $HCO_3^-$ in exchange for intracellular $Cl^-$ (FIGS. 3 and 4). NCBE is functionally distinct from so far reported anion exchangers and $Na^+$-$HCO_3^-$ cotransporters. This is because: 1) NCBE, expressed in *Xenopus laevis*, exhibited a $Na^+$ uptake increase dependent on intracellular $Cl^-$, 2) it shows the ability of exporting Cl⁻ out of the cells, and, furthermore, 3) the NCBE, expressed in HEK239 cells, elevates intracellular pH in a manner dependent upon extracellular Na⁺ and $HCO_3^-$, and intracellular Cl⁻. These properties are similar to those of Na⁺-driven Cl⁻/$HCO_3^-$ exchanger described in native cells. The cloned NCBE, therefore, is concluded to be a Na⁺-driven Cl⁻/$HCO_3^-$ exchanger.

Possible physiological relevance of NCBE.

That NCBE mRNA is expressed in insulin secreting cell line MIN6 and pancreatic islets implies its physiological relevance. It has been shown that glucose-induced insulin secretion is accompanied by a rise in intracellular pH in pancreatic β-cells. While several intracellular pH regulators have been suggested to be present in pancreatic β-cells, their molecular basis has not been known so far. NCBE is the first intracellular pH-regulating exchanger whose primary structure and functional properties have been determined. NCBE most likely contributes to the process for recovery of intracellular pH in pancreatic β-cells that have been acidified by glucose metabolism. NCBE mRNA occurs also in the testis, although its expression level is low. It has been shown that intracellular pH regulates many functions in sperm including sperm capacitation. As sperm capacitation results in the increase in intracellular pH, which requires functional Na⁺, Cl⁻ and $HCO_3^-$-dependent acid-efflux pathway, NCBE could participate in the process of sperm capacitation. NCBE mRNA is also expressed at high levels in the brain. Though physiological studies suggests that NCBE is present in hippocampal neurons and astrocytes, its physiological significance of such cells remains unknown at present.

What is claimed is:

1. A cell in which a protein comprising the amino acid sequence set forth as SEQ IDS NO:2 or NO:4 in the Sequence Listing is expressed, wherein the cell is of a species different from the species of origin of the proteins.

2. A method for selection of agonists and antagonists of sodium ion-driven chloride/bicarbonate exchanger, which method comprises bringing the cell of claim 1 into contact with a candidate compound, measuring the function of the sodium ion-driven chloride/bicarbonate exchanger, comparing the result thus obtained with a result obtained by measuring the function of the sodium ion-driven chloride/bicarbonate exchanger of the cell of claim 1 which has not been brought into contact with the candidate compound, and thereby determining whether or not the candidate compound enhances or inhibits the function.

3. A cell in which a protein is expressed comprising an amino acid sequence having deletion, substitution, addition or insertion of one to three amino acids relative to the amino acid sequence set forth as SEQ ID NO:2 or NO:4 in the Sequence Listing, which protein, when expressed in a cell, functions sodium ion-driven chloride/bicarbonate exchanger, and wherein the cell is of a species different from the species of origin of the protein consisting of the amino acid sequence set forth as SEQ ID NO: 2 or SEQ ID NO: 4.

4. A method for selection of agonists and antagonists of sodium ion-driven chloride/bicarbonate exchanger, which method comprises bringing the cell of claim 3 into contact with a candidate compound, measuring the function of the sodium ion-driven chloride/bicarbonate exchanger, comparing the result thus obtained with a result obtained by measuring the function of the sodium ion-driven chloride/bicarbonate exchanger of the cell of claim 2 which has not been brought into contact with the candidate compound, and thereby determining whether or not the candidate compound enhances or inhibits the function.

5. The cell according to claim 3 wherein the sodium ion-driven chloride/bicarbonate exchanger, dependently upon both of extracellular bicarbonate and intracellular chloride ions, takes up extracellular sodium ion into the cell and transports intracellular sodium ion out of the cell.

6. A method for selection of agonists and antagonists of sodium ion-driven chloride/bicarbonate exchanger, which method comprises bringing the cell of claim 5 into contact with a candidate compound, measuring the function of the sodium ion-driven chloride/bicarbonate exchanger, comparing the result thus obtained with a result obtained by measuring the function of the sodium ion-driven chloride/bicarbonate exchanger of the cell of claim 3 which has not been brought into contact with the candidate compound, and thereby determining whether or not the candidate compound enhances or inhibits the function.

7. An isolated DNA comprising the nucleotide sequence set forth as SEQ ID NO:1 or NO:3 in the Sequence Listing.

8. An isolated DNA comprising a nucleotide sequence consisting of the nucleotides 67 through 3330 in the nucleotide sequence set forth as SEQ ID NO21 in the Sequence Listing.

9. An isolated DNA comprising a nucleotide sequence consisting of the nucleotides 83 through 3346 in the nucleotide sequence set forth as SEQ ID NO:3 in the Sequence Listing.

10. An isolated DNA comprising a nucleotide sequence having deletion, substitution, addition or insertion of one to ten nucleotides relative to a DNA comprising a nucleotide sequence consisting of the nucleotides 67 through 3330 in the nucleotide sequence set forth as SEQ ID NO:1 in the Sequence Listing, and encoding:
 (1) a protein comprising the amino acid sequence set forth as SEQ ID NO:2 in the Sequence Listing, or
 (2) a protein comprising an amino acid sequence having deletion, substitution, addition or insertion of one to three amino acids relative to the amino acid sequence set forth as SEQ ID NO:2 in the Sequence Listing, which protein, when expressed in a cell, functions as sodium ion-driven chloride/bicarbonate exchanger.

11. An isolated DNA comprising a nucleotide sequence having deletion, substitution, addition or insertion of one to ten nucleotides relative to a DNA comprising a nucleotide sequence consisting of the nucleotides 83 through 3346 in the nucleotide sequence set forth as SEQ ID NO:3 in the Sequence Listing, and encoding:
 (1) a protein comprising the amino acid sequence set forth as SEQ ID NO:4 in the Sequence Listing, or
 (2) a protein comprising an amino acid sequence having deletion, substitution, addition or insertion of one to three amino acids relative to the amino acid sequence set forth as SEQ ID NO:4 in the Sequence Listing, which protein, when expressed in a cell, functions as sodium ion-driven chloride/bicarbonate exchanger.

* * * * *

SEQUENCE LISTING

```
<160> NUMBER OF SEQ ID NOS: 8

<210> SEQ ID NO 1
<211> LENGTH: 5385
<212> TYPE: DNA
<213> ORGANISM: Mus musculus

<400> SEQUENCE: 1
ggctgagtgg aagacactga agacactgca gagcaaggtg ctttttttcc agaggtgtta      60 cagaac atg gag att aaa gac cag gga gcc caa atg gag ccg ctg ctg       108
       Met Glu Ile Lys Asp Gln Gly Ala Gln Met Glu Pro Leu Leu
        1               5                  10 cct acg aga aat gat gaa gaa gcc gtt gtg gat aga ggt gga aca cgc      156
Pro Thr Arg Asn Asp Glu Glu Ala Val Val Asp Arg Gly Gly Thr Arg
15                  20                  25                  30 tct att ctc aaa aca cat ttt gag aaa gaa gat tta gaa ggt cat cgg      204
Ser Ile Leu Lys Thr His Phe Glu Lys Glu Asp Leu Glu Gly His Arg
                35                  40                  45 aca tta ttt att gga gtt cat gtg ccc ctg ggt gga aga aaa agc cat      252
Thr Leu Phe Ile Gly Val His Val Pro Leu Gly Gly Arg Lys Ser His
            50                  55                  60 cgt cgt cac agg cat cgt ggt cat aag cac aga aag agg gac aga gag      300
Arg Arg His Arg His Arg Gly His Lys His Arg Lys Arg Asp Arg Glu
65                  70                  75 aga gat tcg gga ctg gag gat gga aga gag tcc cct tct ttt gac acc      348
Arg Asp Ser Gly Leu Glu Asp Gly Arg Glu Ser Pro Ser Phe Asp Thr
    80                  85                  90 cca tcg cag agg gtg cag ttt att ctt gga act gag gac gat gat gag      396
Pro Ser Gln Arg Val Gln Phe Ile Leu Gly Thr Glu Asp Asp Asp Glu
95                 100                 105                 110 gag cac ctc cct cat gac ctt ttc aca gag ctg gat gag att tgc tgg      444
Glu His Leu Pro His Asp Leu Phe Thr Glu Leu Asp Glu Ile Cys Trp
                115                 120                 125 cgt gaa ggg gaa gat gct gag tgg cga gag aca gcc agg tgg ttg aaa      492
Arg Glu Gly Glu Asp Ala Glu Trp Arg Glu Thr Ala Arg Trp Leu Lys
            130                 135                 140 ttt gaa gag gat gtg gaa gat gga gga gaa aga tgg agt aag ccc tat      540
Phe Glu Glu Asp Val Glu Asp Gly Gly Glu Arg Trp Ser Lys Pro Tyr
            145                 150                 155 gtg gcc acg ctt tca tta cac agc ttg ttt gag ttg aga agc tgc atc      588
Val Ala Thr Leu Ser Leu His Ser Leu Phe Glu Leu Arg Ser Cys Ile
160                 165                 170
```

```
ctg aat gga act gtg cta ctg gac atg cat gcc aac acg ata gaa gaa    636
Leu Asn Gly Thr Val Leu Leu Asp Met His Ala Asn Thr Ile Glu Glu
175                 180                 185                 190 att gca gat atg gtc ctt gac cag cag gtc agc tca ggc cag ctg aat    684
Ile Ala Asp Met Val Leu Asp Gln Gln Val Ser Ser Gly Gln Leu Asn
                    195                 200                 205 gaa gat gtt cgc cac agg gtc cac gaa gca ttg atg aag cag cat cat    732
Glu Asp Val Arg His Arg Val His Glu Ala Leu Met Lys Gln His His
                210                 215                 220 cac cag aat cag aaa aaa ctg gct aac agg att cct att gtc cga tct    780
His Gln Asn Gln Lys Lys Leu Ala Asn Arg Ile Pro Ile Val Arg Ser
            225                 230                 235 ttg gct gat att ggc aag aaa caa tca gaa cca aat tcc atg gat aaa    828
Leu Ala Asp Ile Gly Lys Lys Gln Ser Glu Pro Asn Ser Met Asp Lys
        240                 245                 250 aat gca ggt cag gtt gtt tct cct cag tct gct cca gcc tgt gct gag    876
Asn Ala Gly Gln Val Val Ser Pro Gln Ser Ala Pro Ala Cys Ala Glu
255                 260                 265                 270 aat aaa aat gat gtc agc agg gaa aac agc act gta gac ttc agc aag    924
Asn Lys Asn Asp Val Ser Arg Glu Asn Ser Thr Val Asp Phe Ser Lys
                    275                 280                 285 gtt gat ctg cat ttt atg aaa aag att cct ccg ggt gct gaa gct tca    972
Val Asp Leu His Phe Met Lys Lys Ile Pro Pro Gly Ala Glu Ala Ser
                290                 295                 300 aac atc ttg gta gga gaa ctg gag ttc cta gac aga gct gtg gtt gcc   1020
Asn Ile Leu Val Gly Glu Leu Glu Phe Leu Asp Arg Ala Val Val Ala
            305                 310                 315 ttt gtc agg ttg tct cca gct gtc ttg ctc caa gga ctt gct gaa gtt   1068
Phe Val Arg Leu Ser Pro Ala Val Leu Leu Gln Gly Leu Ala Glu Val
        320                 325                 330 cca atc cca agc aga ttt ctg ttc atc ctt ctg gga ccc ctg gga aag   1116
Pro Ile Pro Ser Arg Phe Leu Phe Ile Leu Leu Gly Pro Leu Gly Lys
335                 340                 345                 350 ggt caa cag tac cac gag att ggc aga tcg att gcg acc tta atg act   1164
Gly Gln Gln Tyr His Glu Ile Gly Arg Ser Ile Ala Thr Leu Met Thr
                    355                 360                 365 gat gag gtg ttt cat gat gtt gct tac aaa gct aaa gac cgc aat gac   1212
Asp Glu Val Phe His Asp Val Ala Tyr Lys Ala Lys Asp Arg Asn Asp
                370                 375                 380 ttg gta tca gga att gat gag ttt ctg gat cag gtt acc gtt ctt cct   1260
Leu Val Ser Gly Ile Asp Glu Phe Leu Asp Gln Val Thr Val Leu Pro
            385                 390                 395 cct gga gaa tgg gat cca agc ata cga ata gaa cct ccc aaa aat gtc   1308
Pro Gly Glu Trp Asp Pro Ser Ile Arg Ile Glu Pro Pro Lys Asn Val
        400                 405                 410 cct tcc cag gag aag agg aag att cct gct gta cca aat gga aca gca   1356
Pro Ser Gln Glu Lys Arg Lys Ile Pro Ala Val Pro Asn Gly Thr Ala
415                 420                 425                 430 gct cat ggc gaa gct gag cca cat gga gga cac agc gga cct gaa ctc   1404
Ala His Gly Glu Ala Glu Pro His Gly Gly His Ser Gly Pro Glu Leu
                    435                 440                 445 cag cga act ggg agg att ttt ggg gga ctt atg tta gat atc aaa aga   1452
Gln Arg Thr Gly Arg Ile Phe Gly Gly Leu Met Leu Asp Ile Lys Arg
                450                 455                 460 aag gct cca ttc ttc tgg agc gac ttc agg gat gct ttc agc ctg cag   1500
Lys Ala Pro Phe Phe Trp Ser Asp Phe Arg Asp Ala Phe Ser Leu Gln
            465                 470                 475 tgc tta gca tcg ttc ctg ttt ctc tac tgt gca tgc atg tct cct gtc   1548
Cys Leu Ala Ser Phe Leu Phe Leu Tyr Cys Ala Cys Met Ser Pro Val
```

-continued

```
        480                 485                 490
atc aca ttt gga gga ctg ttg gga gaa gca act gaa ggt cgt ata agt    1596
Ile Thr Phe Gly Gly Leu Leu Gly Glu Ala Thr Glu Gly Arg Ile Ser
495                 500                 505                 510 gca atc gaa tca ctc ttt gga gca tct atg acc ggg ata gcc tat tct    1644
Ala Ile Glu Ser Leu Phe Gly Ala Ser Met Thr Gly Ile Ala Tyr Ser
                515                 520                 525 ctt ttt ggt gga cag ccc ctg acc ata tta ggc agc aca gga cct gtt    1692
Leu Phe Gly Gly Gln Pro Leu Thr Ile Leu Gly Ser Thr Gly Pro Val
            530                 535                 540 ttg gtg ttt gaa aag atc ttg ttt aag ttt tgc aag gaa tac ggc ctg    1740
Leu Val Phe Glu Lys Ile Leu Phe Lys Phe Cys Lys Glu Tyr Gly Leu
        545                 550                 555 tcg tac ttg tcc tta cgg gcc agc att ggg ctc tgg act gca aca ctg    1788
Ser Tyr Leu Ser Leu Arg Ala Ser Ile Gly Leu Trp Thr Ala Thr Leu
    560                 565                 570 tgc atc atc ctt gtg gcc acg gac gcg agc tca ctc gtc tgc tac atc    1836
Cys Ile Ile Leu Val Ala Thr Asp Ala Ser Ser Leu Val Cys Tyr Ile
575                 580                 585                 590 acc cgg ttt acc gaa gag gct ttt gct tct ctc att tgc atc att ttt    1884
Thr Arg Phe Thr Glu Glu Ala Phe Ala Ser Leu Ile Cys Ile Ile Phe
                595                 600                 605 atc tat gaa gcc ctg gag aag ttg ttt gag ctc agt gaa acc tat cca    1932
Ile Tyr Glu Ala Leu Glu Lys Leu Phe Glu Leu Ser Glu Thr Tyr Pro
            610                 615                 620 atc aat atg cac aat gat ttg gaa ctg ctg aca caa tac tca tgt aac    1980
Ile Asn Met His Asn Asp Leu Glu Leu Leu Thr Gln Tyr Ser Cys Asn
        625                 630                 635 tgt atg gag cca cat agt ccc agc aat gac aca ctg aag gaa tgg cgg    2028
Cys Met Glu Pro His Ser Pro Ser Asn Asp Thr Leu Lys Glu Trp Arg
    640                 645                 650 gag tcc aac ctt tct gcc tct gac ata atc tgg ggg aac cta act gtg    2076
Glu Ser Asn Leu Ser Ala Ser Asp Ile Ile Trp Gly Asn Leu Thr Val
655                 660                 665                 670 tca gag tgc aga tca ctg cac ggg gag tat gtc ggg cga gcc tgt ggc    2124
Ser Glu Cys Arg Ser Leu His Gly Glu Tyr Val Gly Arg Ala Cys Gly
                675                 680                 685 cat ggc cac ccc tac gtg cca gat gtt ctc ttc tgg tcg gtg atc ctg    2172
His Gly His Pro Tyr Val Pro Asp Val Leu Phe Trp Ser Val Ile Leu
            690                 695                 700 ttc ttc tcc aca gtt acc atg tca gcc acc ctg aag cag ttc aag acc    2220
Phe Phe Ser Thr Val Thr Met Ser Ala Thr Leu Lys Gln Phe Lys Thr
        705                 710                 715 agc cgc tat ttc cca acc aag gtt cga tcc ata gtg agt gat ttt gcg    2268
Ser Arg Tyr Phe Pro Thr Lys Val Arg Ser Ile Val Ser Asp Phe Ala
    720                 725                 730 gtt ttt ctt aca att ctg tgt atg gtt tta att gac tat gcc att ggg    2316
Val Phe Leu Thr Ile Leu Cys Met Val Leu Ile Asp Tyr Ala Ile Gly
735                 740                 745                 750 atc cca tca cca aaa cta caa gta cca agc gtt ttc aag ccg acc ata    2364
Ile Pro Ser Pro Lys Leu Gln Val Pro Ser Val Phe Lys Pro Thr Ile
                755                 760                 765 tac gac cgt ggc tgg ttt gtt aca cct ttg ggt cca aac cca tgg tgg    2412
Tyr Asp Arg Gly Trp Phe Val Thr Pro Leu Gly Pro Asn Pro Trp Trp
            770                 775                 780 aca atc ata gct gcc atc atc cca gct tta ctc tgt act att ctg att    2460
Thr Ile Ile Ala Ala Ile Ile Pro Ala Leu Leu Cys Thr Ile Leu Ile
        785                 790                 795 ttc atg gac cag cag att aca gct gtc atc atc aac aga aaa gag cac    2508
```

```
              Phe Met Asp Gln Gln Ile Thr Ala Val Ile Ile Asn Arg Lys Glu His
                  800                 805                 810 aag cta aag aaa ggt tgt ggc tat cac ctg gat ctg tta atg gtg gca        2556
Lys Leu Lys Lys Gly Cys Gly Tyr His Leu Asp Leu Leu Met Val Ala
815                 820                 825                 830 gtc atg ctc ggg gtc tgc tcc att atg ggc ctg cca tgg ttt gtg gct        2604
Val Met Leu Gly Val Cys Ser Ile Met Gly Leu Pro Trp Phe Val Ala
                835                 840                 845 gcc aca gtt ctc tcc atc act cat gtc aac agc ctc aag ctc gaa tca        2652
Ala Thr Val Leu Ser Ile Thr His Val Asn Ser Leu Lys Leu Glu Ser
                    850                 855                 860 gag tgc tct gct cca gga gaa caa ccc aag ttt ctc ggc att cgg gag        2700
Glu Cys Ser Ala Pro Gly Glu Gln Pro Lys Phe Leu Gly Ile Arg Glu
865                 870                 875 cag agg gtg acc ggg ctc atg att ttt att ctt atg ggt tca tcc gtt        2748
Gln Arg Val Thr Gly Leu Met Ile Phe Ile Leu Met Gly Ser Ser Val
    880                 885                 890 ttc atg acc agc att ctg aag ttt atc ccc atg cca gtg tta tac gga        2796
Phe Met Thr Ser Ile Leu Lys Phe Ile Pro Met Pro Val Leu Tyr Gly
895                 900                 905                 910 gtg ttt ctt tat atg ggt gct tcg tct ctc aaa gga att cag tta ttt        2844
Val Phe Leu Tyr Met Gly Ala Ser Ser Leu Lys Gly Ile Gln Leu Phe
                915                 920                 925 gat aga ata aag ctc ttc tgg atg cca gcc aaa cat caa cca gat ttc        2892
Asp Arg Ile Lys Leu Phe Trp Met Pro Ala Lys His Gln Pro Asp Phe
                    930                 935                 940 atc tat cta agg cac gtg ccc ctc cgg aaa gtc cat ctc ttc aca gtc        2940
Ile Tyr Leu Arg His Val Pro Leu Arg Lys Val His Leu Phe Thr Val
945                 950                 955 att cag atg agt tgt ctc ggc ctt ctg tgg ata atc aaa gtt tcg aga        2988
Ile Gln Met Ser Cys Leu Gly Leu Leu Trp Ile Ile Lys Val Ser Arg
    960                 965                 970 gct gct att gtc ttt cct atg atg gtg ttg gca cta gtg ttt gtg aga        3036
Ala Ala Ile Val Phe Pro Met Met Val Leu Ala Leu Val Phe Val Arg
975                 980                 985                 990 aag ttg atg gac ttc ttg ttt acc aaa cgg gaa ctc agc tgg ctt gat        3084
Lys Leu Met Asp Phe Leu Phe Thr Lys Arg Glu Leu Ser Trp Leu Asp
                995                 1000                1005 gat tta atg cct gag agt aaa aag aag aaa ctt gaa gat gct gag aaa        3132
Asp Leu Met Pro Glu Ser Lys Lys Lys Lys Leu Glu Asp Ala Glu Lys
                1010                1015                1020 gaa gaa gaa caa agt atg cta gcc atg gag gac gag ggc aca gta caa        3180
Glu Glu Glu Gln Ser Met Leu Ala Met Glu Asp Glu Gly Thr Val Gln
            1025                1030                1035 ctc cca ctg gag gga cac tac aga gac gac ccg tct gtg atc aat att        3228
Leu Pro Leu Glu Gly His Tyr Arg Asp Asp Pro Ser Val Ile Asn Ile
        1040                1045                1050 tct gat gaa atg tca aag act gcc atg tgg ggg aac ctt cta gtt act        3276
Ser Asp Glu Met Ser Lys Thr Ala Met Trp Gly Asn Leu Leu Val Thr
1055                1060                1065                1070 gct gac aac tca aaa gaa aag gag tca cgc ttt cct tct aaa agc tcc        3324
Ala Asp Asn Ser Lys Glu Lys Glu Ser Arg Phe Pro Ser Lys Ser Ser
                1075                1080                1085 cct tcc taa tcactctaga agctgattcc ccaaagcaat gaaagccgaa aggagaa       3380
Pro Ser
gaaagctgac tcagggaaag gcgttgacag ggagacttgt ctatgacttg atcttcaatt     3440 tatttttac atatatatat atgagaagag tgtcacaatt attaacaaaa ctgctttgat      3500
catgtaattg taaccctctc ctcccatccc accttcatac tgtaagtagt gcaagccttc    3560
```

-continued

| | |
|---|---|
| attctatttc tgtgttcagc ctctgagcag gtcgacaccc ttgtaagcag atccaatagc | 3620 |
| taatgcaaga gtctccagtg ttactgccgt aagacattcg ccaacacagg attctcattg | 3680 |
| ttgacattaa gagaacaaag cttcctttaa aagataagtt atatttgcct agtttgtatt | 3740 |
| ttcctacctt agtaacctga agatgcctga taattttatt cagaagaatt ttgaaaggta | 3800 |
| gtcgtacttt ttatttttta tggcttagca ttcgttactg gttttgaaag acccaaatca | 3860 |
| aaaagttact ctgaaagcat ttttaataat tgtatttatg tatttccttg acttaatatg | 3920 |
| aaacatttaa tacttaataa ctgttacttc aagtcatttg agaaagagac ctgttcatat | 3980 |
| cttcttaaaa gacatactgc aaagagtcaa gtagtgttca cttagaattc aagttgtaac | 4040 |
| catgcagtca aaaactaggc ttgtattaaa tgctttagag atatttgaag agttttgtgg | 4100 |
| ggcttttcat tttaaatctt taccagaaat atgctactga gtttctctcc cattgacaag | 4160 |
| ggttgcttcc cgaataagcc tatgacatac atacttacgg aatgccacat ggtgcaacat | 4220 |
| tgtacatttg atgccagccc tggcagctgt tctgctgacc atggtcatgt gctgctaagt | 4280 |
| ttggttccta tcatgttgtc atgttagacc aacaggtctc caactgtatt ttgtttttt | 4340 |
| tgcaaagctc ttttccacat tttaactaaa tgcatgttgt ggaaaaatag tctttgaaat | 4400 |
| aaaatttcag attttgttag aaaaggttat gtaaatactt cagtccatat gaaacagttc | 4460 |
| aactttattg aaacaggaag gagattatgg attttttgagt attactaaat ataaatttca | 4520 |
| tttaattttc aataaatgtg ctttaataca aaacaaaata tcatagggggt cttagttcct | 4580 |
| aaaaaagtat caatgattaa caaccttata atctttcaat gtccaggttt agaaaaattc | 4640 |
| agagccttct gggttttata aattacatgt actctgtgta aatacacata attagaaaaa | 4700 |
| tcctctttgc ttttaagcta atgaagacga gagacaacag agcctacata accttaatat | 4760 |
| tctgatatct tgaacaaaaa atttcctcag aatcctttca ggagccattt ttttaatgag | 4820 |
| atatgagcca aaattgtgag aagaattttc agttcgtaaa gtctgtatt ataaatggta | 4880 |
| aagaaaaatg caaaattctt ttccaaatgt gctacctttg tgatagttgt aatagcgaca | 4940 |
| ctctctctaa acattctcgc tgtctatgac ttagcaggcc aatccccaaa gcactctcct | 5000 |
| ggtgtctcta gagtgtcatg tctgttctgt tgaaatgacc agtgagtgac acttcacatg | 5060 |
| atcactggtt taaacaggca atcagcctat gaaattctgt atttctgaat attttatag | 5120 |
| taattttgtt cttgtgtgaa ttttaatgct atctctatct taatcttaat attttgaaat | 5180 |
| cacataaaat ataagaaaat gtagtattct atatttactc taatttcaga ttcctggtca | 5240 |
| aaattactga atatcttgaa tgtaatttat tgcaatgttt aagtactgtg taaatgtgac | 5300 |
| aggatattgt gttttcaaa actaagaaat gttatgtgga aataaatatt tatcctaaaa | 5360 |
| aaaaaaaaaa aaaaaaaaa aaaaa | 5385 |

<210> SEQ ID NO 2
<211> LENGTH: 1088
<212> TYPE: PRT
<213> ORGANISM: Mus musculus

<400> SEQUENCE: 2

Met Glu Ile Lys Asp Gln Gly Ala Gln Met Glu Pro Leu Leu Pro Thr
1               5                   10                  15

Arg Asn Asp Glu Glu Ala Val Val Asp Arg Gly Gly Thr Arg Ser Ile
            20                  25                  30

Leu Lys Thr His Phe Glu Lys Glu Asp Leu Glu Gly His Arg Thr Leu
        35                  40                  45

-continued

Phe Ile Gly Val His Val Pro Leu Gly Gly Arg Lys Ser His Arg Arg
50                  55                  60

His Arg His Arg Gly His Lys His Arg Lys Arg Asp Arg Glu Arg Asp
65                  70                  75                  80

Ser Gly Leu Glu Asp Gly Arg Glu Ser Pro Ser Phe Asp Thr Pro Ser
                85                  90                  95

Gln Arg Val Gln Phe Ile Leu Gly Thr Glu Asp Asp Asp Glu Glu His
                100                 105                 110

Leu Pro His Asp Leu Phe Thr Glu Leu Asp Glu Ile Cys Trp Arg Glu
            115                 120                 125

Gly Glu Asp Ala Glu Trp Arg Glu Thr Ala Arg Trp Leu Lys Phe Glu
        130                 135                 140

Glu Asp Val Glu Asp Gly Gly Glu Arg Trp Ser Lys Pro Tyr Val Ala
145                 150                 155                 160

Thr Leu Ser Leu His Ser Leu Phe Glu Leu Arg Ser Cys Ile Leu Asn
                165                 170                 175

Gly Thr Val Leu Leu Asp Met His Ala Asn Thr Ile Glu Glu Ile Ala
                180                 185                 190

Asp Met Val Leu Asp Gln Gln Val Ser Ser Gly Gln Leu Asn Glu Asp
            195                 200                 205

Val Arg His Arg Val His Glu Ala Leu Met Lys Gln His His His Gln
210                 215                 220

Asn Gln Lys Lys Leu Ala Asn Arg Ile Pro Ile Val Arg Ser Leu Ala
225                 230                 235                 240

Asp Ile Gly Lys Lys Gln Ser Glu Pro Asn Ser Met Asp Lys Asn Ala
                245                 250                 255

Gly Gln Val Val Ser Pro Gln Ser Ala Pro Ala Cys Ala Glu Asn Lys
                260                 265                 270

Asn Asp Val Ser Arg Glu Asn Ser Thr Val Asp Phe Ser Lys Val Asp
            275                 280                 285

Leu His Phe Met Lys Lys Ile Pro Pro Gly Ala Glu Ala Ser Asn Ile
        290                 295                 300

Leu Val Gly Glu Leu Glu Phe Leu Asp Arg Ala Val Val Ala Phe Val
305                 310                 315                 320

Arg Leu Ser Pro Ala Val Leu Leu Gln Gly Leu Ala Glu Val Pro Ile
                325                 330                 335

Pro Ser Arg Phe Leu Phe Ile Leu Leu Gly Pro Leu Gly Lys Gly Gln
                340                 345                 350

Gln Tyr His Glu Ile Gly Arg Ser Ile Ala Thr Leu Met Thr Asp Glu
            355                 360                 365

Val Phe His Asp Val Ala Tyr Lys Ala Lys Asp Arg Asn Asp Leu Val
        370                 375                 380

Ser Gly Ile Asp Glu Phe Leu Asp Gln Val Thr Val Leu Pro Pro Gly
385                 390                 395                 400

Glu Trp Asp Pro Ser Ile Arg Ile Glu Pro Lys Asn Val Pro Ser
                405                 410                 415

Gln Glu Lys Arg Lys Ile Pro Ala Val Pro Asn Gly Thr Ala Ala His
            420                 425                 430

Gly Glu Ala Glu Pro His Gly Gly His Ser Gly Pro Glu Leu Gln Arg
        435                 440                 445

Thr Gly Arg Ile Phe Gly Gly Leu Met Leu Asp Ile Lys Arg Lys Ala
    450                 455                 460

Pro Phe Phe Trp Ser Asp Phe Arg Asp Ala Phe Ser Leu Gln Cys Leu

```
                465                 470                 475                 480
Ala Ser Phe Leu Phe Leu Tyr Cys Ala Cys Met Ser Pro Val Ile Thr
                    485                 490                 495
Phe Gly Gly Leu Leu Gly Glu Ala Thr Glu Gly Arg Ile Ser Ala Ile
                    500                 505                 510
Glu Ser Leu Phe Gly Ala Ser Met Thr Gly Ile Ala Tyr Ser Leu Phe
                    515                 520                 525
Gly Gly Gln Pro Leu Thr Ile Leu Gly Ser Thr Gly Pro Val Leu Val
                    530                 535                 540
Phe Glu Lys Ile Leu Phe Lys Phe Cys Lys Glu Tyr Gly Leu Ser Tyr
545                 550                 555                 560
Leu Ser Leu Arg Ala Ser Ile Gly Leu Trp Thr Ala Thr Leu Cys Ile
                    565                 570                 575
Ile Leu Val Ala Thr Asp Ala Ser Ser Leu Val Cys Tyr Ile Thr Arg
                    580                 585                 590
Phe Thr Glu Glu Ala Phe Ala Ser Leu Ile Cys Ile Ile Phe Ile Tyr
                    595                 600                 605
Glu Ala Leu Glu Lys Leu Phe Glu Leu Ser Glu Thr Tyr Pro Ile Asn
                    610                 615                 620
Met His Asn Asp Leu Glu Leu Leu Thr Gln Tyr Ser Cys Asn Cys Met
625                 630                 635                 640
Glu Pro His Ser Pro Ser Asn Asp Thr Leu Lys Glu Trp Arg Glu Ser
                    645                 650                 655
Asn Leu Ser Ala Ser Asp Ile Ile Trp Gly Asn Leu Thr Val Ser Glu
                    660                 665                 670
Cys Arg Ser Leu His Gly Glu Tyr Val Gly Arg Ala Cys Gly His Gly
                    675                 680                 685
His Pro Tyr Val Pro Asp Val Leu Phe Trp Ser Val Ile Leu Phe Phe
                    690                 695                 700
Ser Thr Val Thr Met Ser Ala Thr Leu Lys Gln Phe Lys Thr Ser Arg
705                 710                 715                 720
Tyr Phe Pro Thr Lys Val Arg Ser Ile Val Ser Asp Phe Ala Val Phe
                    725                 730                 735
Leu Thr Ile Leu Cys Met Val Leu Ile Asp Tyr Ala Ile Gly Ile Pro
                    740                 745                 750
Ser Pro Lys Leu Gln Val Pro Ser Val Phe Lys Pro Thr Ile Tyr Asp
                    755                 760                 765
Arg Gly Trp Phe Val Thr Pro Leu Gly Pro Asn Pro Trp Trp Thr Ile
                    770                 775                 780
Ile Ala Ala Ile Ile Pro Ala Leu Leu Cys Thr Ile Leu Ile Phe Met
785                 790                 795                 800
Asp Gln Gln Ile Thr Ala Val Ile Ile Asn Arg Lys Glu His Lys Leu
                    805                 810                 815
Lys Lys Gly Cys Gly Tyr His Leu Asp Leu Leu Met Val Ala Val Met
                    820                 825                 830
Leu Gly Val Cys Ser Ile Met Gly Leu Pro Trp Phe Val Ala Ala Thr
                    835                 840                 845
Val Leu Ser Ile Thr His Val Asn Ser Leu Lys Leu Glu Ser Glu Cys
                    850                 855                 860
Ser Ala Pro Gly Glu Gln Pro Lys Phe Leu Gly Ile Arg Glu Gln Arg
865                 870                 875                 880
Val Thr Gly Leu Met Ile Phe Ile Leu Met Gly Ser Ser Val Phe Met
                    885                 890                 895
```

```
Thr Ser Ile Leu Lys Phe Ile Pro Met Pro Val Leu Tyr Gly Val Phe
        900                 905                 910

Leu Tyr Met Gly Ala Ser Ser Leu Lys Gly Ile Gln Leu Phe Asp Arg
        915                 920                 925

Ile Lys Leu Phe Trp Met Pro Ala Lys His Gln Pro Asp Phe Ile Tyr
        930                 935                 940

Leu Arg His Val Pro Leu Arg Lys Val His Leu Phe Thr Val Ile Gln
945                 950                 955                 960

Met Ser Cys Leu Gly Leu Leu Trp Ile Ile Lys Val Ser Arg Ala Ala
                965                 970                 975

Ile Val Phe Pro Met Met Val Leu Ala Leu Val Phe Val Arg Lys Leu
        980                 985                 990

Met Asp Phe Leu Phe Thr Lys Arg Glu Leu Ser Trp Leu Asp Asp Leu
        995                 1000                1005

Met Pro Glu Ser Lys Lys Lys Leu Glu Asp Ala Glu Lys Glu Glu
        1010                1015                1020

Glu Gln Ser Met Leu Ala Met Glu Asp Glu Gly Thr Val Gln Leu Pro
1025                1030                1035                1040

Leu Glu Gly His Tyr Arg Asp Asp Pro Ser Val Ile Asn Ile Ser Asp
                1045                1050                1055

Glu Met Ser Lys Thr Ala Met Trp Gly Asn Leu Leu Val Thr Ala Asp
                1060                1065                1070

Asn Ser Lys Glu Lys Glu Ser Arg Phe Pro Ser Lys Ser Ser Pro Ser
                1075                1080                1085

<210> SEQ ID NO 3
<211> LENGTH: 4138
<212> TYPE: DNA
<213> ORGANISM: Homo sapience

<400> SEQUENCE: 3
taagcagagc gagtgccggg ctgagtgtaa gacactgaag acactgcaga gcaaggtgct      60
tattccagag gcgttacaaa ac atg gag att aaa gac cag gga gcc caa atg     112
                          Met Glu Ile Lys Asp Gln Gly Ala Gln Met
                            1               5                  10 gag ccg ctg ctg cct acg aga aat gat gaa gaa gca gtt gtg gat aga     160
Glu Pro Leu Leu Pro Thr Arg Asn Asp Glu Glu Ala Val Val Asp Arg
                15                  20                  25 ggt gga act cgt tct att ctc aaa aca cac ttt gag aaa gaa gat tta     208
Gly Gly Thr Arg Ser Ile Leu Lys Thr His Phe Glu Lys Glu Asp Leu
        30                  35                  40 gaa ggt cat cga aca cta ttt att gga gta cat gtg ccc ttg gga gga     256
Glu Gly His Arg Thr Leu Phe Ile Gly Val His Val Pro Leu Gly Gly
    45                  50                  55 aga aaa agc cat cga cgt cac agg cat cgt ggt cat aaa cac aga aag     304
Arg Lys Ser His Arg Arg His Arg His Arg Gly His Lys His Arg Lys
60                  65                  70 aga gac aga gaa aga gat tca gga tta gag gat gga agg gag tca cct     352
Arg Asp Arg Glu Arg Asp Ser Gly Leu Glu Asp Gly Arg Glu Ser Pro
75                  80                  85                  90 tct ttt gac acc cca tca cag agg gta cag ttt att ctt gga acc gag     400
Ser Phe Asp Thr Pro Ser Gln Arg Val Gln Phe Ile Leu Gly Thr Glu
                95                  100                 105 gat gat gac gag gaa cac att cct cat gac ctt ttc aca gaa ctg gat     448
Asp Asp Asp Glu Glu His Ile Pro His Asp Leu Phe Thr Glu Leu Asp
                110                 115                 120
```

```
gag att tgt tgg cgt gaa ggt gag gac gct gag tgg cga gaa aca gcc         496
Glu Ile Cys Trp Arg Glu Gly Glu Asp Ala Glu Trp Arg Glu Thr Ala
        125                 130                 135 agg tgg ttg aag ttt gaa gaa gat gtg gaa gat gga gga gaa agg tgg         544
Arg Trp Leu Lys Phe Glu Glu Asp Val Glu Asp Gly Gly Glu Arg Trp
140                 145                 150 agc aag cct tat gtg gct act ctt tca ttg cac agc ttg ttt gaa ttg         592
Ser Lys Pro Tyr Val Ala Thr Leu Ser Leu His Ser Leu Phe Glu Leu
155                 160                 165                 170 aga agt tgt att ctg aat gga act gtg ttg ctg gac atg cat gcc aac         640
Arg Ser Cys Ile Leu Asn Gly Thr Val Leu Leu Asp Met His Ala Asn
            175                 180                 185 act tta gaa gaa att gca gat atg gtt ctt gac caa caa gtg agc tca         688
Thr Leu Glu Glu Ile Ala Asp Met Val Leu Asp Gln Gln Val Ser Ser
        190                 195                 200 ggt cag ctg aat gaa gat gta cgc cat agg gtc cat gag gca ttg atg         736
Gly Gln Leu Asn Glu Asp Val Arg His Arg Val His Glu Ala Leu Met
    205                 210                 215 aaa cag cat cat cat cag aat cag aaa aaa ctc acc aac agg att ccc         784
Lys Gln His His His Gln Asn Gln Lys Lys Leu Thr Asn Arg Ile Pro
220                 225                 230 att gtt cgt tcc ttt gct gat att ggc aag aaa cag tca gaa cca aat         832
Ile Val Arg Ser Phe Ala Asp Ile Gly Lys Lys Gln Ser Glu Pro Asn
235                 240                 245                 250 tcc atg gac aaa aat gca ggt cag gtt gtt tct cct cag tct gct cca         880
Ser Met Asp Lys Asn Ala Gly Gln Val Val Ser Pro Gln Ser Ala Pro
                255                 260                 265 gcc tgt gtt gaa aat aaa aat gat gtt agc aga gaa aac agc act gtt         928
Ala Cys Val Glu Asn Lys Asn Asp Val Ser Arg Glu Asn Ser Thr Val
            270                 275                 280 gac ttt agc aag gtt gat ctg cat ttt atg aaa aag att cct cca ggt         976
Asp Phe Ser Lys Val Asp Leu His Phe Met Lys Lys Ile Pro Pro Gly
        285                 290                 295 gct gaa gca tcg aac atc tta ctg gga gaa ctg gag ttc ttg gat cga        1024
Ala Glu Ala Ser Asn Ile Leu Leu Gly Glu Leu Glu Phe Leu Asp Arg
    300                 305                 310 aca gta gtt gcg ttt gtc agg ttg tct cca gct gta ttg ctt caa gga        1072
Thr Val Val Ala Phe Val Arg Leu Ser Pro Ala Val Leu Leu Gln Gly
315                 320                 325                 330 ctg gct gaa gtc cca atc cca acc aga ttt ttg ttc att ctt ctg gga        1120
Leu Ala Glu Val Pro Ile Pro Thr Arg Phe Leu Phe Ile Leu Leu Gly
                335                 340                 345 ccc ctg gga aag ggt caa cag tac cat gag att ggc aga tca att gca        1168
Pro Leu Gly Lys Gly Gln Gln Tyr His Glu Ile Gly Arg Ser Ile Ala
            350                 355                 360 acc cta atg aca gat gag gta ttt cat gat gtt gcc tat aaa gct aaa        1216
Thr Leu Met Thr Asp Glu Val Phe His Asp Val Ala Tyr Lys Ala Lys
        365                 370                 375 gat cgt aat gac ttg gta tca gga att gat gag ttt ctg gat cag gtt        1264
Asp Arg Asn Asp Leu Val Ser Gly Ile Asp Glu Phe Leu Asp Gln Val
    380                 385                 390 act gtt ctc cct cct gga gaa tgg gat cca agc att cga ata gag cct        1312
Thr Val Leu Pro Pro Gly Glu Trp Asp Pro Ser Ile Arg Ile Glu Pro
395                 400                 405                 410 ccc aaa aat gtt cct tcc cag gag aag agg aag att cct gct gta cca        1360
Pro Lys Asn Val Pro Ser Gln Glu Lys Arg Lys Ile Pro Ala Val Pro
                415                 420                 425 aat gga aca gca gct cat ggg gaa gca gag ccc cac gga gga cat agt        1408
Asn Gly Thr Ala Ala His Gly Glu Ala Glu Pro His Gly Gly His Ser
            430                 435                 440
```

-continued

```
gga cct gaa ctc cag cga act gga agg att ttt ggg gga ctt att tta      1456
Gly Pro Glu Leu Gln Arg Thr Gly Arg Ile Phe Gly Gly Leu Ile Leu
        445                 450                 455 gat atc aaa aga aaa gct cca tac ttc tgg agt gac ttc aga gat gct      1504
Asp Ile Lys Arg Lys Ala Pro Tyr Phe Trp Ser Asp Phe Arg Asp Ala
460                 465                 470 ttc agc ctg cag tgc tta gca tct ttt cta ttt ctc tac tgc gcg tgt      1552
Phe Ser Leu Gln Cys Leu Ala Ser Phe Leu Phe Leu Tyr Cys Ala Cys
475                 480                 485                 490 atg tct cct gtc atc acg ttt gga gga ctg ctg gga gaa gca act gaa      1600
Met Ser Pro Val Ile Thr Phe Gly Gly Leu Leu Gly Glu Ala Thr Glu
            495                 500                 505 ggg cgt ata agt gca att gaa tct ctc ttt gga gca tcc atg acc ggg      1648
Gly Arg Ile Ser Ala Ile Glu Ser Leu Phe Gly Ala Ser Met Thr Gly
        510                 515                 520 ata gcc tat tct ctc ttt ggt gga cag cct ctt acc ata tta ggc agt      1696
Ile Ala Tyr Ser Leu Phe Gly Gly Gln Pro Leu Thr Ile Leu Gly Ser
                525                 530                 535 aca gga cca gtt ttg gtg ttt gaa aag att ttg ttt aaa ttt tgc aaa      1744
Thr Gly Pro Val Leu Val Phe Glu Lys Ile Leu Phe Lys Phe Cys Lys
540                 545                 550 gaa tat ggg ctg tca tac cta tct tta aga gct agc att gga ctt tgg      1792
Glu Tyr Gly Leu Ser Tyr Leu Ser Leu Arg Ala Ser Ile Gly Leu Trp
555                 560                 565                 570 act gca act cta tgt atc ata ctt gtg gcc aca gat gct agt tcc ctt      1840
Thr Ala Thr Leu Cys Ile Ile Leu Val Ala Thr Asp Ala Ser Ser Leu
            575                 580                 585 gtc tgc tac atc act cgg ttt act gaa gaa gct ttt gct tcc ctg att      1888
Val Cys Tyr Ile Thr Arg Phe Thr Glu Glu Ala Phe Ala Ser Leu Ile
        590                 595                 600 tgc atc att ttc att tat gag gcc ctg gag aag ttg ttt gaa ctc agt      1936
Cys Ile Ile Phe Ile Tyr Glu Ala Leu Glu Lys Leu Phe Glu Leu Ser
                605                 610                 615 gaa gca tat cca atc aac atg cat aat gat ctg gaa ctg ctg aca caa      1984
Glu Ala Tyr Pro Ile Asn Met His Asn Asp Leu Glu Leu Leu Thr Gln
620                 625                 630 tac tcg tgt aac tgt gtg gaa ccg cat aat ccc agc aat ggc aca ttg      2032
Tyr Ser Cys Asn Cys Val Glu Pro His Asn Pro Ser Asn Gly Thr Leu
635                 640                 645                 650 aag gaa tgg agg gaa tcc aat att tct gcc tct gac ata att tgg gag      2080
Lys Glu Trp Arg Glu Ser Asn Ile Ser Ala Ser Asp Ile Ile Trp Glu
            655                 660                 665 aac cta act gtg tca gaa tgc aaa tca ttg cat gga gag tat gtt gga      2128
Asn Leu Thr Val Ser Glu Cys Lys Ser Leu His Gly Glu Tyr Val Gly
        670                 675                 680 cgg gcc tgt ggc cat gat cac cca tat gtt cca gat gtt cta ttt tgg      2176
Arg Ala Cys Gly His Asp His Pro Tyr Val Pro Asp Val Leu Phe Trp
                685                 690                 695 tct gtg atc ctg ttc ttt tcc aca gtt act ctg tca gcc acc ctg aag      2224
Ser Val Ile Leu Phe Phe Ser Thr Val Thr Leu Ser Ala Thr Leu Lys
700                 705                 710 cag ttc aag act agc aga tat ttt cca acc aag gtt cga tcc ata gtg      2272
Gln Phe Lys Thr Ser Arg Tyr Phe Pro Thr Lys Val Arg Ser Ile Val
715                 720                 725                 730 agt gac ttt gct gtc ttt ctt aca att ctg tgt atg gtt tta att gac      2320
Ser Asp Phe Ala Val Phe Leu Thr Ile Leu Cys Met Val Leu Ile Asp
            735                 740                 745 tat gcc att ggg atc cca tct cca aaa cta caa gta cca agt gtt ttc      2368
Tyr Ala Ile Gly Ile Pro Ser Pro Lys Leu Gln Val Pro Ser Val Phe
```

|     |     |
| --- | --- |
| aag ccc act aga gat gat cgt ggc tgg ttt gtt acg cct tta ggt cca<br>Lys Pro Thr Arg Asp Asp Arg Gly Trp Phe Val Thr Pro Leu Gly Pro<br>        765                          770                       775 | 2416 |
| aac cca tgg tgg aca gta ata gct gct ata att cca gct ctg ctt tgt<br>Asn Pro Trp Trp Thr Val Ile Ala Ala Ile Ile Pro Ala Leu Leu Cys<br>    780                          785                        790 | 2464 |
| act att cta att ttc atg gac caa cag att aca gct gtc atc atc aac<br>Thr Ile Leu Ile Phe Met Asp Gln Gln Ile Thr Ala Val Ile Ile Asn<br>795                          800                        805                        810 | 2512 |
| agg aaa gag cat aag cta aag aaa ggt tgt ggg tac cat ctg gac cta<br>Arg Lys Glu His Lys Leu Lys Lys Gly Cys Gly Tyr His Leu Asp Leu<br>               815                          820                        825 | 2560 |
| tta atg gtg gct gtc atg ctc ggt gta tgc tcc atc atg ggc ctg cca<br>Leu Met Val Ala Val Met Leu Gly Val Cys Ser Ile Met Gly Leu Pro<br>    830                          835                        840 | 2608 |
| tgg ttt gtg gct gcc aca gtc ctc tcc atc act cat gtc aat agc cta<br>Trp Phe Val Ala Ala Thr Val Leu Ser Ile Thr His Val Asn Ser Leu<br>        845                        850                        855 | 2656 |
| aaa ctg gaa tca gaa tgc tca gct cca gga gaa caa ccc aaa ttt ctc<br>Lys Leu Glu Ser Glu Cys Ser Ala Pro Gly Glu Gln Pro Lys Phe Leu<br>860                          865                        870 | 2704 |
| ggc att cgg gag caa agg gtt act ggg ctt atg att ttt att ctt atg<br>Gly Ile Arg Glu Gln Arg Val Thr Gly Leu Met Ile Phe Ile Leu Met<br>875                        880                        885                        890 | 2752 |
| ggt tca tca gtc ttt atg acc agt att ctg aag ttt att ccc atg cca<br>Gly Ser Ser Val Phe Met Thr Ser Ile Leu Lys Phe Ile Pro Met Pro<br>        895                        900                        905 | 2800 |
| gtg cta tat gga gtg ttt ctt tat atg ggt gct tca tct cta aag gga<br>Val Leu Tyr Gly Val Phe Leu Tyr Met Gly Ala Ser Ser Leu Lys Gly<br>              910                          915                        920 | 2848 |
| att cag ttc ttt gat agg ata aag ctc ttc tgg atg ccg gca aaa cat<br>Ile Gln Phe Phe Asp Arg Ile Lys Leu Phe Trp Met Pro Ala Lys His<br>        925                        930                        935 | 2896 |
| caa cca gat ttt ata tac cta agg cac gta ccg ctt cga aaa gtg cat<br>Gln Pro Asp Phe Ile Tyr Leu Arg His Val Pro Leu Arg Lys Val His<br>940                          945                        950 | 2944 |
| ctc ttc aca att att cag atg agt tgc ctt ggc ctt ttg tgg ata ata<br>Leu Phe Thr Ile Ile Gln Met Ser Cys Leu Gly Leu Leu Trp Ile Ile<br>955                          960                        965                        970 | 2992 |
| aaa gtt tca aga gct gct att gtc tct ccc atg atg gtg tta tcc ctg<br>Lys Val Ser Arg Ala Ala Ile Val Ser Pro Met Met Val Leu Ser Leu<br>              975                          980                        985 | 3040 |
| gtt ttt gta aga aag ttg atg gac ttg ttg ttc acg aaa cgg gaa ctc<br>Val Phe Val Arg Lys Leu Met Asp Leu Leu Phe Thr Lys Arg Glu Leu<br>        990                        995                        1000 | 3088 |
| tgc tgg ttg gat gat ttg atg cct gag agt aag aaa aag aaa ctg gaa<br>Cys Trp Leu Asp Asp Leu Met Pro Glu Ser Lys Lys Lys Lys Leu Glu<br>              1005                        1010                        1015 | 3136 |
| tat gct gaa aaa gaa gaa gaa caa tgt gtg cta cct atg gaa gat gag<br>Tyr Ala Glu Lys Glu Glu Glu Gln Cys Val Leu Pro Met Glu Asp Glu<br>        1020                        1025                        1030 | 3184 |
| ggc aca gta caa ctc cca ttg gaa ggg cac tat aga gat gat cca tct<br>Gly Thr Val Gln Leu Pro Leu Glu Gly His Tyr Arg Asp Asp Pro Ser<br>1035                        1040                        1045                        1050 | 3232 |
| gtg atc aat ata tct gat gaa atg tca aag act gcc ttg tgg agg aac<br>Val Ile Asn Ile Ser Asp Glu Met Ser Lys Thr Ala Leu Trp Arg Asn<br>              1055                        1060                        1065 | 3280 |
| ctt ctg att act gcc gat aac tca aaa gat aag gag tca agc ttt cct | 3328 |

-continued

| | | |
|---|---|---|
| Leu Leu Ile Thr Ala Asp Asn Ser Lys Asp Lys Glu Ser Ser Phe Pro<br>              1070                1075                1080 | | |
| tcc aaa agc tcc cct tcc taa tcactctaga agctgattcc ccaaagcatt<br>Ser Lys Ser Ser Pro Ser<br>        1085 | 3379 | |
| gaaagccgaa aagagaagaa agctgactca gggatagttg ttgacaggga gacttgtcta | 3439 | |
| tgactcgatc ttcaatttat tttttacata tatatgagaa gagtgtcaca attattaata | 3499 | |
| aaactgcttg gatcatgtat ggtaaattct gtccctcaac ccaaatccac tttcatacgg | 3559 | |
| taagtagggc aaaacttgtt tcatttcggt gttaaaattt cggagcagga gacatccctg | 3619 | |
| tgagcagaaa caatagccaa tgcagaatct gtgtgttcct tgctgaacgt aagacatttg | 3679 | |
| taaactggat tctgattgtc agttttatga gagcaatagc ttccttaaag agataagtca | 3739 | |
| tatacaccta gtttgtattc tcatacttta gagacctgaa gacgcctgat aatttcattc | 3799 | |
| aggagaattt ttgaaaggta gtcaaacttc ttttttagttt ttatagctta gcattagtga | 3859 | |
| cttatttcaa aagacccaaa tcaaaaagtt agtttgaaag catttttttaa taattgtatt | 3919 | |
| tatgcatttg gctactgtaa gttttgctcc atggaataat gatgtgatag caaaaatgaa | 3979 | |
| taagactatg aataagttcc tacatgaagg ttaatgtcag tggtgaaaaa tcttattatg | 4039 | |
| ctccaatata ctgccagcat gctgagtata cttggatcat aaaaaactgt tcatttttc | 4099 | |
| ttatttattt tatgcatagg aatattcatt ccggaattc | 4138 | |

<210> SEQ ID NO 4
<211> LENGTH: 1088
<212> TYPE: PRT
<213> ORGANISM: Homo sapience

<400> SEQUENCE: 4

Met Glu Ile Lys Asp Gln Gly Ala Gln Met Glu Pro Leu Leu Pro Thr
1               5                   10                  15

Arg Asn Asp Glu Glu Ala Val Val Asp Arg Gly Gly Thr Arg Ser Ile
            20                  25                  30

Leu Lys Thr His Phe Glu Lys Glu Asp Leu Glu Gly His Arg Thr Leu
        35                  40                  45

Phe Ile Gly Val His Val Pro Leu Gly Gly Arg Lys Ser His Arg Arg
    50                  55                  60

His Arg His Arg Gly His Lys His Arg Lys Arg Asp Arg Glu Arg Asp
65                  70                  75                  80

Ser Gly Leu Glu Asp Gly Arg Glu Ser Pro Ser Phe Asp Thr Pro Ser
                85                  90                  95

Gln Arg Val Gln Phe Ile Leu Gly Thr Glu Asp Asp Asp Glu Glu His
            100                 105                 110

Ile Pro His Asp Leu Phe Thr Glu Leu Asp Glu Ile Cys Trp Arg Glu
        115                 120                 125

Gly Glu Asp Ala Glu Trp Arg Glu Thr Ala Arg Trp Leu Lys Phe Glu
    130                 135                 140

Glu Asp Val Glu Asp Gly Gly Glu Arg Trp Ser Lys Pro Tyr Val Ala
145                 150                 155                 160

Thr Leu Ser Leu His Ser Leu Phe Glu Leu Arg Ser Cys Ile Leu Asn
                165                 170                 175

Gly Thr Val Leu Leu Asp Met His Ala Asn Thr Leu Glu Glu Ile Ala
            180                 185                 190

Asp Met Val Leu Asp Gln Gln Val Ser Ser Gly Gln Leu Asn Glu Asp
        195                 200                 205

-continued

```
Val Arg His Arg Val His Glu Ala Leu Met Lys Gln His His His Gln
    210                 215                 220
Asn Gln Lys Lys Leu Thr Asn Arg Ile Pro Ile Val Arg Ser Phe Ala
225                 230                 235                 240
Asp Ile Gly Lys Lys Gln Ser Glu Pro Asn Ser Met Asp Lys Asn Ala
                245                 250                 255
Gly Gln Val Val Ser Pro Gln Ser Ala Pro Ala Cys Val Glu Asn Lys
                260                 265                 270
Asn Asp Val Ser Arg Glu Asn Ser Thr Val Asp Phe Ser Lys Val Asp
                275                 280                 285
Leu His Phe Met Lys Lys Ile Pro Pro Gly Ala Glu Ala Ser Asn Ile
    290                 295                 300
Leu Leu Gly Glu Leu Glu Phe Leu Asp Arg Thr Val Val Ala Phe Val
305                 310                 315                 320
Arg Leu Ser Pro Ala Val Leu Leu Gln Gly Leu Ala Glu Val Pro Ile
                325                 330                 335
Pro Thr Arg Phe Leu Phe Ile Leu Leu Gly Pro Leu Gly Lys Gly Gln
                340                 345                 350
Gln Tyr His Glu Ile Gly Arg Ser Ile Ala Thr Leu Met Thr Asp Glu
        355                 360                 365
Val Phe His Asp Val Ala Tyr Lys Ala Lys Asp Arg Asn Asp Leu Val
    370                 375                 380
Ser Gly Ile Asp Glu Phe Leu Asp Gln Val Thr Val Leu Pro Pro Gly
385                 390                 395                 400
Glu Trp Asp Pro Ser Ile Arg Ile Glu Pro Pro Lys Asn Val Pro Ser
                405                 410                 415
Gln Glu Lys Arg Lys Ile Pro Ala Val Pro Asn Gly Thr Ala Ala His
                420                 425                 430
Gly Glu Ala Glu Pro His Gly Gly His Ser Gly Pro Glu Leu Gln Arg
        435                 440                 445
Thr Gly Arg Ile Phe Gly Gly Leu Ile Leu Asp Ile Lys Arg Lys Ala
    450                 455                 460
Pro Tyr Phe Trp Ser Asp Phe Arg Asp Ala Phe Ser Leu Gln Cys Leu
465                 470                 475                 480
Ala Ser Phe Leu Phe Leu Tyr Cys Ala Cys Met Ser Pro Val Ile Thr
                485                 490                 495
Phe Gly Gly Leu Leu Gly Glu Ala Thr Glu Gly Arg Ile Ser Ala Ile
                500                 505                 510
Glu Ser Leu Phe Gly Ala Ser Met Thr Gly Ile Ala Tyr Ser Leu Phe
        515                 520                 525
Gly Gly Gln Pro Leu Thr Ile Leu Gly Ser Thr Gly Pro Val Leu Val
    530                 535                 540
Phe Glu Lys Ile Leu Phe Lys Phe Cys Lys Glu Tyr Gly Leu Ser Tyr
545                 550                 555                 560
Leu Ser Leu Arg Ala Ser Ile Gly Leu Trp Thr Ala Thr Leu Cys Ile
                565                 570                 575
Ile Leu Val Ala Thr Asp Ala Ser Ser Leu Val Cys Tyr Ile Thr Arg
                580                 585                 590
Phe Thr Glu Glu Ala Phe Ala Ser Leu Ile Cys Ile Ile Phe Ile Tyr
        595                 600                 605
Glu Ala Leu Glu Lys Leu Phe Glu Leu Ser Glu Ala Tyr Pro Ile Asn
    610                 615                 620
```

-continued

```
Met His Asn Asp Leu Glu Leu Leu Thr Gln Tyr Ser Cys Asn Cys Val
625                 630                 635                 640

Glu Pro His Asn Pro Ser Asn Gly Thr Leu Lys Glu Trp Arg Glu Ser
            645                 650                 655

Asn Ile Ser Ala Ser Asp Ile Ile Trp Glu Asn Leu Thr Val Ser Glu
                660                 665                 670

Cys Lys Ser Leu His Gly Glu Tyr Val Gly Arg Ala Cys Gly His Asp
            675                 680                 685

His Pro Tyr Val Pro Asp Val Leu Phe Trp Ser Val Ile Leu Phe Phe
        690                 695                 700

Ser Thr Val Thr Leu Ser Ala Thr Leu Lys Gln Phe Lys Thr Ser Arg
705                 710                 715                 720

Tyr Phe Pro Thr Lys Val Arg Ser Ile Val Ser Asp Phe Ala Val Phe
                725                 730                 735

Leu Thr Ile Leu Cys Met Val Leu Ile Asp Tyr Ala Ile Gly Ile Pro
            740                 745                 750

Ser Pro Lys Leu Gln Val Pro Ser Val Phe Lys Pro Thr Arg Asp Asp
        755                 760                 765

Arg Gly Trp Phe Val Thr Pro Leu Gly Pro Asn Pro Trp Trp Thr Val
    770                 775                 780

Ile Ala Ala Ile Ile Pro Ala Leu Leu Cys Thr Ile Leu Ile Phe Met
785                 790                 795                 800

Asp Gln Gln Ile Thr Ala Val Ile Ile Asn Arg Lys Glu His Lys Leu
                805                 810                 815

Lys Lys Gly Cys Gly Tyr His Leu Asp Leu Leu Met Val Ala Val Met
            820                 825                 830

Leu Gly Val Cys Ser Ile Met Gly Leu Pro Trp Phe Val Ala Ala Thr
        835                 840                 845

Val Leu Ser Ile Thr His Val Asn Ser Leu Lys Leu Glu Ser Glu Cys
850                 855                 860

Ser Ala Pro Gly Glu Gln Pro Lys Phe Leu Gly Ile Arg Glu Gln Arg
865                 870                 875                 880

Val Thr Gly Leu Met Ile Phe Ile Leu Met Gly Ser Ser Val Phe Met
                885                 890                 895

Thr Ser Ile Leu Lys Phe Ile Pro Met Pro Val Leu Tyr Gly Val Phe
            900                 905                 910

Leu Tyr Met Gly Ala Ser Ser Leu Lys Gly Ile Gln Phe Phe Asp Arg
        915                 920                 925

Ile Lys Leu Phe Trp Met Pro Ala Lys His Gln Pro Asp Phe Ile Tyr
    930                 935                 940

Leu Arg His Val Pro Leu Arg Lys Val His Leu Phe Thr Ile Ile Gln
945                 950                 955                 960

Met Ser Cys Leu Gly Leu Leu Trp Ile Ile Lys Val Ser Arg Ala Ala
                965                 970                 975

Ile Val Ser Pro Met Met Val Leu Ser Leu Val Phe Val Arg Lys Leu
            980                 985                 990

Met Asp Leu Leu Phe Thr Lys Arg Glu Leu Cys Trp Leu Asp Asp Leu
        995                 1000                1005

Met Pro Glu Ser Lys Lys Lys Leu Glu Tyr Ala Glu Lys Glu Glu
    1010                1015                1020

Glu Gln Cys Val Leu Pro Met Glu Asp Glu Gly Thr Val Gln Leu Pro
1025                1030                1035                1040

Leu Glu Gly His Tyr Arg Asp Asp Pro Ser Val Ile Asn Ile Ser Asp
```

-continued

```
                    1045                1050                1055
Glu Met Ser Lys Thr Ala Leu Trp Arg Asn Leu Leu Ile Thr Ala Asp
                1060                1065                1070

Asn Ser Lys Asp Lys Glu Ser Ser Phe Pro Ser Lys Ser Ser Pro Ser
                1075                1080                1085

<210> SEQ ID NO 5
<211> LENGTH: 19
<212> TYPE: DNA
<213> ORGANISM: Homo sapience

<400> SEQUENCE: 5
tttggagaaa acccctggt                                                19

<210> SEQ ID NO 6
<211> LENGTH: 20
<212> TYPE: DNA
<213> ORGANISM: Homo sapience

<400> SEQUENCE: 6
tgacatcatc caggaagctg                                               20

<210> SEQ ID NO 7
<211> LENGTH: 20
<212> TYPE: DNA
<213> ORGANISM: Homo sapience

<400> SEQUENCE: 7
gtcatgttag accaacaggt                                               20

<210> SEQ ID NO 8
<211> LENGTH: 18
<212> TYPE: DNA
<213> ORGANISM: Homo sapience

<400> SEQUENCE: 8
gttgtaatag cgacactc                                                 18
```